US009821476B2

(12) United States Patent
Zubiate et al.

(10) Patent No.: US 9,821,476 B2
(45) Date of Patent: *Nov. 21, 2017

(54) ARTICULATED DEVICE WITH VISUALIZATION SYSTEM

(71) Applicant: CARNEGIE MELLON UNIVERSITY, Pittsburgh, PA (US)

(72) Inventors: Brett Zubiate, Duxbury, MA (US); Howard Choset, Pittsburgh, PA (US); Amir Degani, Pittsburgh, PA (US); Sarjoun Skaff, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 248 days.

This patent is subject to a terminal disclaimer.

(21) Appl. No.: 14/642,311

(22) Filed: Mar. 9, 2015

(65) Prior Publication Data

US 2015/0239132 A1 Aug. 27, 2015

Related U.S. Application Data

(63) Continuation of application No. 12/937,947, filed as application No. PCT/US2009/040548 on Apr. 14, 2009, now Pat. No. 9,005,114.

(Continued)

(51) Int. Cl.
*A61B 1/008* (2006.01)
*A61B 1/00* (2006.01)
(Continued)

(52) U.S. Cl.
CPC ............... *B25J 18/06* (2013.01); *A61B 1/008* (2013.01); *A61B 1/0053* (2013.01);
(Continued)

(58) Field of Classification Search
CPC ............ A61B 1/00149; A61B 1/00181; A61B 1/0053; A61B 1/0055; A61B 1/008;
(Continued)

(56) References Cited

U.S. PATENT DOCUMENTS 2,987,960 A 6/1961 Sheldon
3,060,972 A 10/1962 Sheldon
(Continued)

FOREIGN PATENT DOCUMENTS

EP 1927312 A1 6/2008
JP S60059214 4/1985
(Continued)

OTHER PUBLICATIONS

Shammas et al., "New Joint Design for Three-dimensional Hyper Redundant Robots," International Conference on Robots and Systems, Las Vegas, NV, Oct. 2003.
(Continued)

*Primary Examiner* — John P Leubecker
(74) *Attorney, Agent, or Firm* — Fox Rothschild LLP

(57) ABSTRACT

An articulated device may include a first steerable multi-linked mechanism and a second steerable multi-linked mechanism. The second steerable multi-linked mechanism may include a first link, a plurality of intermediate links and a second link movably coupled to a second one of the intermediate links. A first one of the intermediate links may be movably coupled to the first link. The articulated device may include a camera located within at least a portion of the second link and a protective shield connected to a distal end of the second link. The protective shield may surround at least a portion of the camera.

8 Claims, 33 Drawing Sheets

Related U.S. Application Data

(60) Provisional application No. 61/044,783, filed on Apr. 14, 2008.

(51) Int. Cl.
*B25J 18/06* (2006.01)
*A61B 1/005* (2006.01)
*H04N 5/372* (2011.01)
*H04N 5/374* (2011.01)
*H04N 7/18* (2006.01)

(52) U.S. Cl.
CPC ........ *A61B 1/0055* (2013.01); *A61B 1/00096* (2013.01); *A61B 1/00142* (2013.01); *A61B 1/00181* (2013.01); *H04N 5/372* (2013.01); *H04N 5/374* (2013.01); *H04N 7/181* (2013.01)

(58) Field of Classification Search
CPC ........ A61B 1/05; A61B 1/00096; B25J 18/06; B25J 19/023
See application file for complete search history.

(56) References Cited

U.S. PATENT DOCUMENTS

| | | |
|---|---|---|
| 3,643,653 A | 2/1972 | Takahashi et al. |
| 3,918,438 A | 11/1975 | Hayamizu et al. |
| 4,838,247 A | 6/1989 | Forkner |
| 4,846,154 A | 7/1989 | MacAnally et al. |
| 4,942,867 A | 7/1990 | Takahashi et al. |
| 5,029,574 A | 7/1991 | Shimamura et al. |
| 5,143,475 A | 9/1992 | Chikama |
| 5,251,611 A | 10/1993 | Zehel et al. |
| 5,253,638 A | 10/1993 | Tamburrino et al. |
| 5,318,526 A | 6/1994 | Cohen |
| 5,327,905 A | 7/1994 | Avitall |
| 5,386,741 A | 2/1995 | Rennex |
| 5,467,763 A | 11/1995 | McMahon et al. |
| 5,472,017 A | 12/1995 | Kovalcheck |
| 5,483,951 A | 1/1996 | Frassica et al. |
| 5,514,157 A | 5/1996 | Nicholas et al. |
| 5,531,715 A | 7/1996 | Engelson et al. |
| 5,549,542 A | 8/1996 | Kovalcheck |
| 5,605,543 A | 2/1997 | Swanson |
| 5,662,587 A | 9/1997 | Grundfest et al. |
| 5,718,663 A | 2/1998 | Wulfsberg |
| 5,743,876 A | 4/1998 | Swanson |
| 5,759,151 A | 6/1998 | Sturges |
| 5,961,445 A | 10/1999 | Chikama |
| 6,036,677 A | 3/2000 | Javier, Jr. et al. |
| 6,197,017 B1 | 3/2001 | Brock et al. |
| 6,221,061 B1 | 4/2001 | Engelson et al. |
| 6,432,112 B2 | 8/2002 | Brock et al. |
| 6,450,104 B1 | 9/2002 | Grant et al. |
| 6,517,477 B1 | 2/2003 | Wendlandt |
| 6,554,844 B2 | 4/2003 | Lee et al. |
| 6,610,007 B2 | 8/2003 | Belson et al. |
| 6,623,448 B2 | 9/2003 | Slater |
| 6,638,266 B2 | 10/2003 | Wilson et al. |
| 6,682,493 B2 | 1/2004 | Mirigian |
| 6,692,430 B2 | 2/2004 | Adler |
| 6,692,485 B1 | 2/2004 | Brock et al. |
| 6,697,048 B2 | 2/2004 | Rosenberg et al. |
| 6,730,020 B2 | 5/2004 | Peng et al. |
| 6,790,173 B2 | 9/2004 | Saadat et al. |
| 6,800,056 B2 | 10/2004 | Tartaglia et al. |
| 6,827,710 B1 | 12/2004 | Mooney et al. |
| 6,837,846 B2 | 1/2005 | Jaffe et al. |
| 6,837,847 B2 | 1/2005 | Ewers et al. |
| 6,858,005 B2 | 2/2005 | Ohline et al. |
| 6,869,396 B2 | 3/2005 | Belson |
| 6,890,297 B2 | 5/2005 | Belson |
| 6,899,673 B2 | 5/2005 | Ogura et al. |
| 6,907,298 B2 | 6/2005 | Smits et al. |
| 6,960,162 B2 | 11/2005 | Saadat et al. |
| 6,960,163 B2 | 11/2005 | Ewers et al. |
| 6,963,792 B1 | 11/2005 | Green |
| 6,974,411 B2 | 12/2005 | Belson |
| 6,976,991 B2 | 12/2005 | Hebert et al. |
| 6,984,203 B2 | 1/2006 | Tartaglia et al. |
| 7,029,435 B2 | 4/2006 | Nakao |
| 7,041,052 B2 | 5/2006 | Saadat et al. |
| 7,044,907 B2 | 5/2006 | Belson |
| 7,087,013 B2 | 8/2006 | Belson et al. |
| 7,090,637 B2 | 8/2006 | Danitz et al. |
| 7,090,683 B2 | 8/2006 | Brock et al. |
| 7,108,688 B2 | 9/2006 | Jensen |
| 7,128,708 B2 | 10/2006 | Saadat et al. |
| 7,137,465 B1 | 11/2006 | Kerrebrock et al. |
| 7,169,141 B2 | 1/2007 | Brock et al. |
| 7,171,279 B2 | 1/2007 | Buckingham et al. |
| 7,182,731 B2 | 2/2007 | Nguyen et al. |
| 7,214,230 B2 | 5/2007 | Brock et al. |
| 7,232,434 B2 | 6/2007 | Suyama et al. |
| 7,250,027 B2 | 7/2007 | Barry |
| 7,322,935 B2 | 1/2008 | Palmer et al. |
| 7,338,505 B2 | 3/2008 | Belson |
| 7,682,319 B2 | 3/2010 | Martin et al. |
| 7,854,109 B2 | 12/2010 | Zubiate et al. |
| 7,931,587 B2 | 4/2011 | Yoshino |
| 2002/0009267 A1 | 1/2002 | Shirakawa |
| 2002/0099267 A1 | 7/2002 | Wendlandt et al. |
| 2003/0032859 A1 | 2/2003 | Belson |
| 2004/0138532 A1 | 7/2004 | Glukhovsky |
| 2004/0236316 A1 | 11/2004 | Danitz et al. |
| 2005/0197531 A1 | 9/2005 | Cabiri et al. |
| 2005/0240078 A1 | 10/2005 | Kwon et al. |
| 2006/0178560 A1 | 8/2006 | Saadat et al. |
| 2007/0043259 A1 | 2/2007 | Jaffe et al. |
| 2007/0219411 A1 | 9/2007 | Dejima et al. |
| 2008/0039690 A1 | 2/2008 | Zubiate et al. |
| 2008/0051631 A1 | 2/2008 | Dejima et al. |
| 2009/0171151 A1 | 7/2009 | Choset et al. |

FOREIGN PATENT DOCUMENTS

| | | |
|---|---|---|
| JP | 2002165756 A | 6/2002 |
| JP | 2005021197 A | 1/2005 |
| WO | WO-2006083306 A2 | 8/2006 |
| WO | WO-2008022114 A2 | 2/2008 |

OTHER PUBLICATIONS

Brown et al., "Design and Control of a Second-Generation Hyper-Redundant Mechanism," International Conference of Robots and Systems, San Diego, CA, Oct. 29-Nov. 2, 2007.

Wolf et al., "A Mobile Hyper Redundant Mechanism for Search and Rescue Tasks," International Conference on Robots and Systems, Las Vegas, NV, Oct. 2003.

ARTICULATED DEVICE WITH VISUALIZATION SYSTEM

CROSS REFERENCE TO RELATED APPLICATIONS

This application claims priority to, and is a continuation of U.S. patent application Ser. No. 12/937,947, filed Mar. 3, 2011, entitled "Articulated Device with Visualization System", which is a national stage application of International Patent Application No. PCT/US2009/040548, filed Apr. 14, 2009, which claims the benefit of U.S. Provisional Application No. 61/044,783 filed on Apr. 14, 2008, the disclosures of which are incorporated herein by reference in their entireties.
Not Applicable

BACKGROUND

This application discloses an invention that is related, generally and in various embodiments, to a multi-linked robotic device, a continuum robot, or other highly articulated device having a visualization system. Typically, physicians and other health care professionals must dispense saline over visualization devices to maintain visibility during surgery and/or other exploratory procedures. However, the visualization device may be used in certain regions, such as cardiac areas, where dispersal of saline is not practical or safe.

SUMMARY

Before the present methods are described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

It must be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. As used herein, the term "comprising" means "including, but not limited to."

In an embodiment, an articulated device may include a first steerable multi-linked mechanism and a second steerable multi-linked mechanism. The second steerable multi-linked mechanism may include a first link, a plurality of intermediate links and a second link movably coupled to a second one of the intermediate links. A first one of the intermediate links may be movably coupled to the first link. The articulated device may include a camera located within at least a portion of the second link and a protective shield connected to a distal end of the second link. The protective shield may surround at least a portion of the camera.

In an embodiment, a visualization system for a steerable multi-linked device may include a first steerable multi-linked mechanism that defines a first plurality of grooves and a second steerable multi-linked mechanism that defines a second plurality of grooves. The second steerable multi-linked mechanism may include a first link, a plurality of intermediate links and a second link movably coupled to a second one of the intermediate links. A first one of the intermediate links may be movably coupled to the first link. The second link may include a protective shield connected to a distal end of the second link. The first plurality of grooves and the second plurality of grooves may cooperate to define one or more working ports along a length of the device. A camera may be located within at least a portion of the second link.

In an embodiment, a visualization system for a steerable multi-linked device may include a steerable multi-linked device. The steerable multi-linked device may include a first steerable multi-linked mechanism that defines a first plurality of grooves, and a second steerable multi-linked mechanism that defines a second plurality of grooves. The first plurality of grooves and the second plurality of grooves may cooperate to define one or more working ports along a length of the device. A camera may be connected to one or more image fibers, and the one or more image fibers may occupy one or more of the working ports.

In an embodiment, a visualization system for a steerable multi-linked device may include a steerable multi-linked device which may include a first steerable multi-linked mechanism that defines a first plurality of grooves, and a second steerable multi-linked mechanism that defines a second plurality of grooves. The first plurality of grooves and the second plurality of grooves may cooperate to define one or more working ports along a length of the device. A camera may be connected to one or more image fibers. The one or more image fibers may be enclosed in a sheath, and the sheath enclosed image fibers may occupy one or more of the working ports.

BRIEF DESCRIPTION OF DRAWINGS

Various embodiments of the invention are described herein by way of example in conjunction with the following figures.

DETAILED DESCRIPTION

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

According to various embodiments, the invention described herein may be utilized to control movement of an articulated device, which in the figures and description herein is described as a steerable multi-linked device. For ease of explanation purposes, the invention will be described in the context of its use with various embodiments of the steerable multi-linked device described herein. However, one skilled in the art will appreciate that the invention may be utilized with other types of multi-linked devices as well as other types of devices such as, but not limited to, endoscopes, highly articulated devices and/or the like.

Figure 1A:
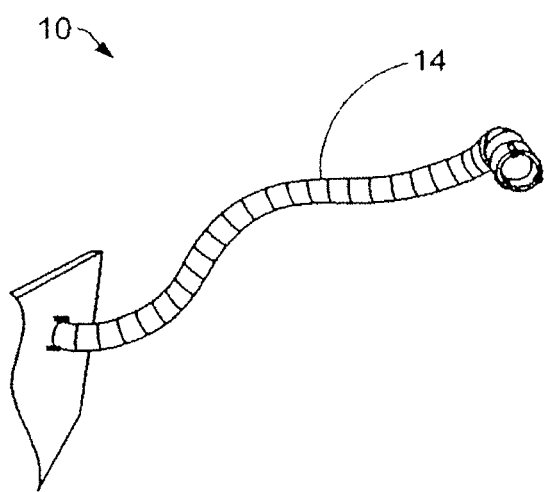
FIGS. 1A and 1B illustrate various embodiments of a steerable multi-linked device.
Figure 1B:
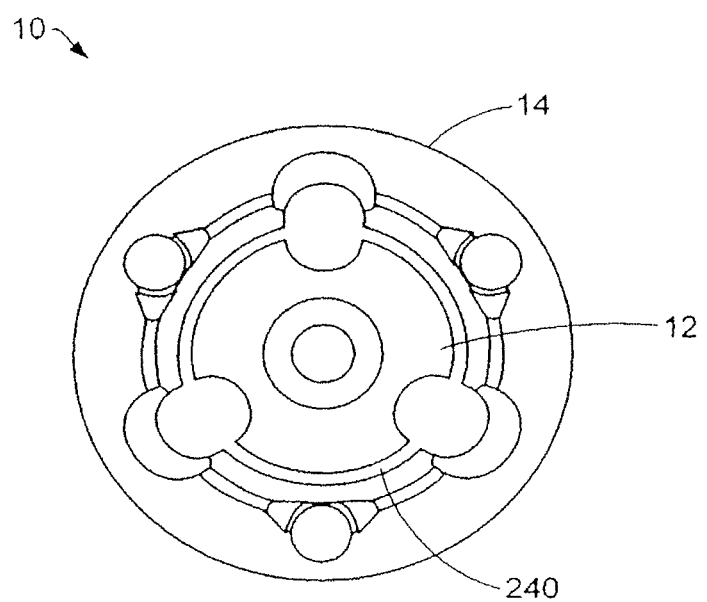

FIGS. 1A and 1B illustrate various embodiments of a highly articulated device 10. According to various embodiments, the device may be a steerable multi-linked device such as a snake-like robot, a continuum robot or the like. Various embodiments of the device 10 may be utilized for medical procedures (e.g., as a robotic bore, positioning device, ablation tool, camera or instrument support, or guidance system for minimally invasive procedures), for surveillance applications, for inspection applications, for search and rescue applications, etc. For purposes of clarity only, the utility of the device 10 will be described hereinbelow in the context of its applicability to medical procedures. However, a person skilled in the art will appreciate that the device 10 can be utilized in a variety of different applications.

The device 10 comprises a first mechanism 12 and a second mechanism 14. According to various embodiments, a mechanism may be a series of articulated links, a snake-like robot, a continuum robot or the like. According to various embodiments, the second mechanism 14 is structured and arranged to receive and surround the first mechanism 12 as shown in FIG. 1B. Thus, the first mechanism and second mechanism may be concentric. For such embodiments, the first mechanism 12 may be considered the inner mechanism or the core mechanism, and the second mechanism 14 may be considered the outer mechanism or the sleeve mechanism. According to other embodiments, the first and second mechanisms 12, 14 may be structured and arranged to have a relationship other than a concentric relationship. For example, one skilled in the art will appreciate that, according to various embodiments, the first and second mechanisms 12, 14 may be structured and arranged to operate in a side-by-side arrangement, where the first mechanism 12 operates adjacent to the second mechanism 14. According to various embodiments, additional and/or alternate configurations may be used within the scope of this disclosure. According to various embodiments, a three-dimensional space 240 may be provided between the first and second mechanisms. This space will be described in more detail below.

As described in more detail hereinbelow, the first mechanism 12 may operate in either a rigid mode or a limp mode, the second mechanism 14 may operate in either a rigid mode or a limp mode, and the first and second mechanisms 12, 14 may operate independent of one another. Both the first mechanism 12 and the second mechanism 14 may be steerable mechanisms. Accordingly, it will be appreciated that the device 10 may be utilized to navigate a luminal space as well as any three-dimensional path within an intracavity space. According to various embodiments, the device 10 may advance by alternating the operation of the first mechanism 12 and the second mechanism 14 between a limp mode and a rigid mode.

Figure 2:
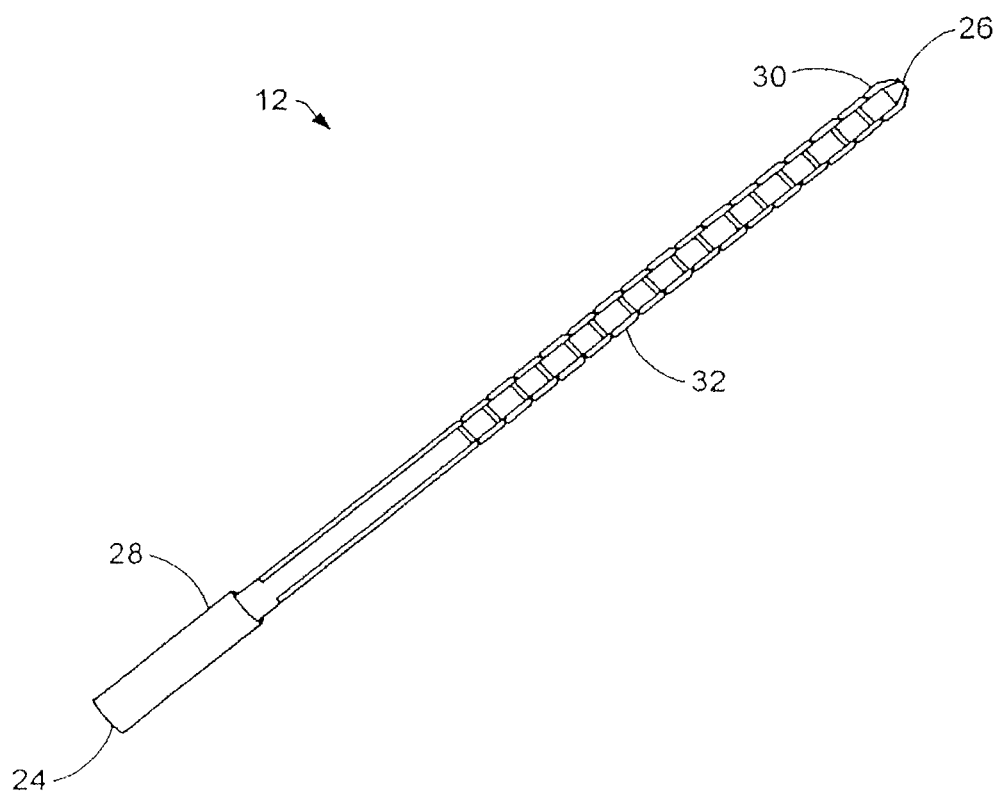
FIG. 2 illustrates various embodiments of a core mechanism of the device of FIG. 1.

According to various embodiments, the device 10 may also comprise one or more cables. According to various embodiments, one or more of the cables may be steering cables and/or tensioning cables. For example, the device may include three cables for steering and tensioning FIG. 2 illustrates various embodiments of the first mechanism 12 of the device 10. The first mechanism 12 is a multi-linked mechanism and includes a first end 24 and a second end 26. The first end 24 may be considered the proximal end and the second end 26 may be considered the distal end. The first mechanism 12 may comprise a first link 28, a second link 30, and one or more intermediate links 32 between the first and second links 28, 30. The first link 28 may be considered the proximal link, and the second link 30 may be considered the distal link.

Figure 3A:
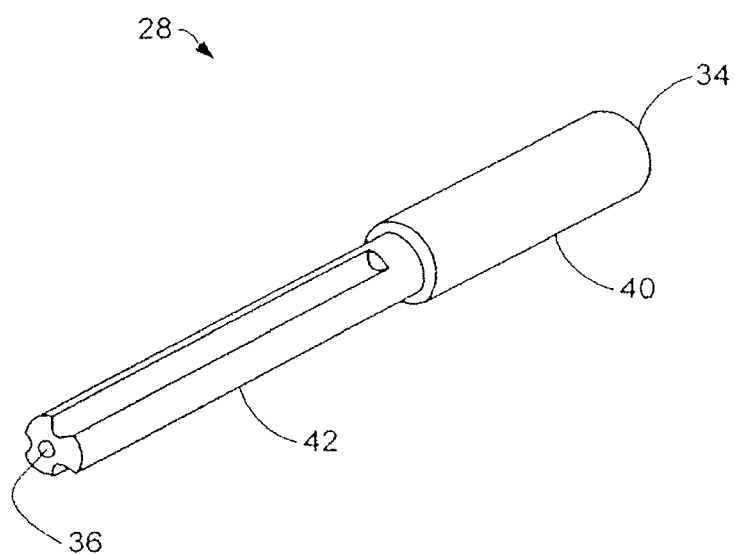
FIGS. 3A-3C illustrate various embodiments of a proximal link of the core mechanism.
Figure 3B:
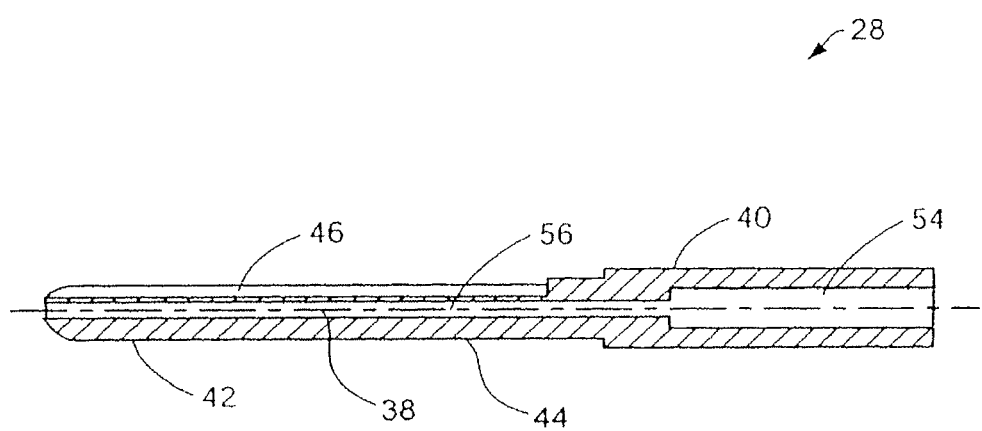
Figure 3C:
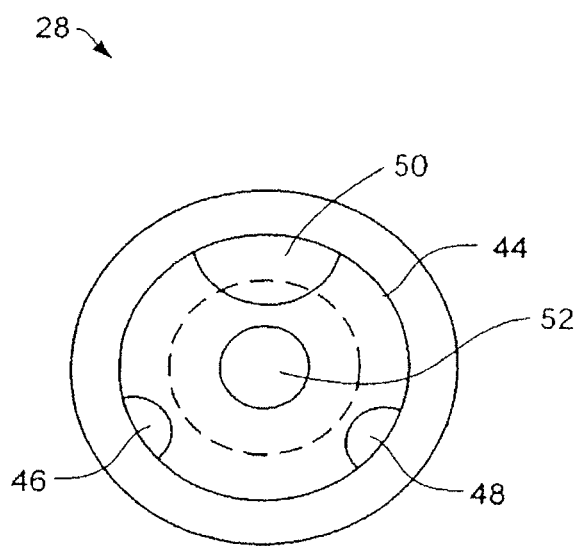

FIGS. 3A-3C illustrate various embodiments of the first link 28 (inner proximal link) of the first mechanism 12. The first link 28 includes a first end 34 and a second end 36, and defines a longitudinal axis 38 that passes through the center of the first end 34 and the center of the second end 36 as shown in FIG. 3B. The first link 28 may be fabricated from any suitable material. According to various embodiments, the first link 28 is fabricated from a fiber reinforced material such as, for example, G10/FR4 Garolite®. The first link 28 has a generally cylindrical shaped exterior and is described in more detail hereinbelow.

The first link 28 comprises a first portion 40 and a second portion 42. The first portion 40 may be considered the proximal portion and the second portion 42 may be considered the distal portion. The first portion 40 may be fabricated integral with the second portion 42. The first portion 40 has a cylindrical shaped exterior, and extends from the first end 34 of the first link 28 toward the second end 36 of the first link 28. According to various embodiments, the diameter of the first portion 40 may be on the order of approximately 6.35 millimeters. Other sizes are possible.

The second portion 42 has a generally cylindrically shaped exterior, with other features described below. The second portion 42 has a cylindrically shaped exterior where it contacts the first portion 40, and tapers toward the second end 36 of the first link 28. The second portion 42 may be shaped in the form of a generally segmented hemisphere at the second end 36 of the first link 28. According to various embodiments, the diameter of the second portion 42 may be on the order of approximately 4.75 millimeters where it contacts the first portion 40. Other sizes are possible.

The second portion 42 comprises a first surface 44. The first surface 44 may be considered the outer surface of the second portion 42. The second portion 42 defines a first groove 46 parallel to the longitudinal axis 38 along the first surface 44, a second groove 48 parallel to the longitudinal axis 38 along the first surface 44, and a third groove 50 parallel to the longitudinal axis 38 along the first surface 44. Each of the first, second and third grooves 46, 48, 50 extend along the first surface 44 toward the second end 36 of the first link 28. The first, second and third grooves 46, 48, 50 may be semi-tubular shaped and may be evenly spaced about the first surface 44 of the second portion 42 of the first link 28 as shown in FIG. 3C. According to various embodiments, the first, second, and third grooves 46, 48, 50 may be configured in the shape of a segmented cylinder. The size of each of the grooves 46, 48, 50 may be identical to one another or may be different from one another. For example, according to various embodiments, the first and second grooves 46, 48 may be configured as segments of a cylinder having a diameter on the order of approximately 1.25 millimeters, and the third groove 50 may be configured as a segment of a cylinder having a diameter on the order of approximately 2.50 millimeters. The length of the first link 28 may be on the order of approximately 65 millimeters. However, one skilled in the art will appreciate that the length or diameter of the first link 28 can vary based on the application.

The first link 28 also defines a passage 52 extending from the first end 34 to the second end 36 along the longitudinal axis 38 as shown in FIG. 3B. The passage 52 is of a size sufficient to allow at least one cable to pass therethrough. According to various embodiments, the passage 52 may be of a sufficient size to allow a tensioning cable to pass therethrough. According to various embodiments, the passage 52 is generally configured as a complex shape that comprises a combination of a first cylinder 54 that extends from the first end 34 toward the second end 36, and a second cylinder 56 that extends from the first cylinder 54 toward the second end 36. The diameter of the first cylinder 54 is larger than the diameter of the second cylinder 56. For example, according to various embodiments, the first cylinder 54 may have a diameter on the order of approximately 3.20 millimeters and the second cylinder 56 may have a diameter on the order of approximately 1.50 millimeters. Other sizes are possible.

Figure 4A:
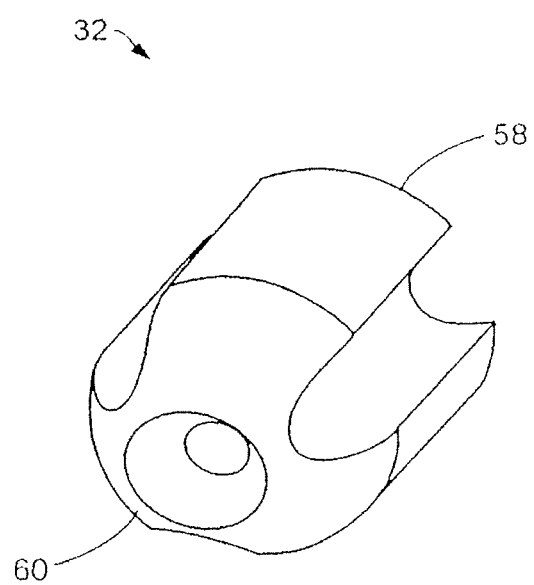
FIGS. 4A-4C illustrate various embodiments of an intermediate link of the core mechanism.
Figure 4B:
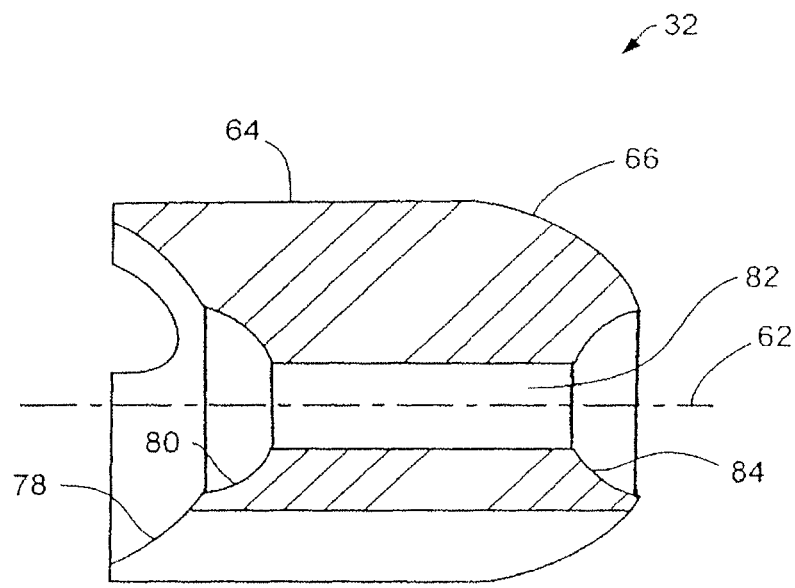
Figure 4C:
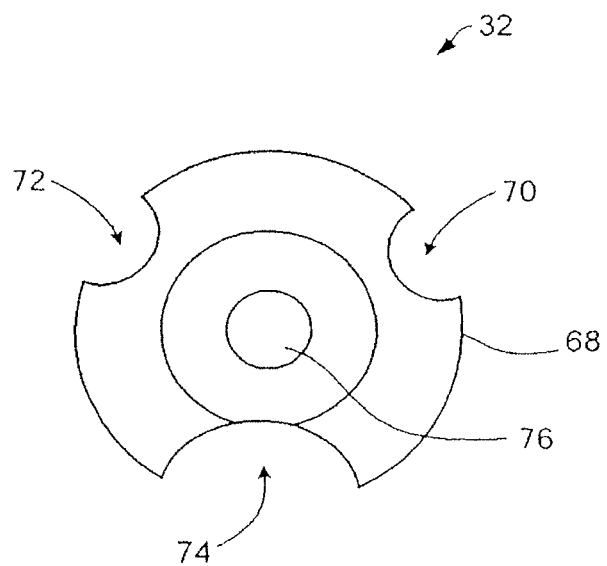

FIGS. 4A-4C illustrate various embodiments of one of the intermediate links 32 (inner intermediate link) of the first mechanism 12. The intermediate link 32 is representative of the other intermediate links 32. The intermediate link 32 includes a first end 58 and a second end 60, and defines a longitudinal axis 62 that passes through the center of the first end 58 and the center of the second end 60 as shown in FIG. 4B. The intermediate link 32 may be fabricated from any suitable material. According to various embodiments, the intermediate link 32 is fabricated from a fiber reinforced material such as, for example, G10/FR4 Garolite®. The intermediate link 32 has a generally bullet-shaped exterior and is described in more detail hereinbelow.

The intermediate link 32 comprises a first portion 64 and a second portion 66. The first portion 64 may be considered the proximal portion and the second portion 66 may be considered the distal portion. The first portion 64 may be fabricated integral with the second portion 66. The first portion 64 has a generally cylindrical shaped exterior, and extends from the first end 58 of the intermediate link 32 toward the second end 60 of the intermediate link 32. According to various embodiments, the second portion 66 has a generally cylindrically shaped exterior where it contacts the first portion 64, and tapers toward the second end 60 of the intermediate link 32. The exterior of the second portion 66 is configured in the form of a generally segmented hemisphere. According to various embodiments, the diameter of the intermediate link 32 may be on the order of approximately 4.75 millimeters at the first end 58 thereof. The length of the intermediate link 32 may be on the order of approximately 5.85 millimeters. However, one skilled in the art will appreciate that the length or diameter of the intermediate link 32 can vary based on the application.

The intermediate link 32 also comprises a first surface 68 that extends from the first end 58 of the intermediate link 32 to the second end 60 of the intermediate link 32. The first surface 68 may be considered the outer surface of the intermediate link 32. The intermediate link 32 also defines a first groove 70 parallel to the longitudinal axis 62 along the first surface 68, a second groove 72 parallel to the longitudinal axis 62 along the first surface 68, and a third groove 74 parallel to the longitudinal axis 62 along the first surface 68. Each of the first, second and third grooves 70, 72, 74 extend along the first surface 68 from the first end 58 of the intermediate link 32 toward the second end 60 of the intermediate link 32. The first, second and third grooves 70, 72, 74 may be semi-tubular shaped and may be evenly spaced about the first surface 68 of the intermediate link 32 as shown in FIG. 4C. According to various embodiments, the first, second, and third grooves 70, 72, 74 may be configured in the shape of a segmented cylinder. The size of each of the grooves 70, 72, 74 may be identical to one another or may be different from one another. For example, according to various embodiments, the first and second grooves 70, 72 are configured as segments of a cylinder having a diameter on the order of approximately 1.75 millimeters at the first end 58 of the intermediate link 32, and the third groove 74 is configured as a segment of a cylinder having a diameter on the order of approximately 2.50 millimeters at the first end 58 of the intermediate link 32. The first, second and third grooves 70, 72, 74 are each configured to receive and partially surround any of a variety of tools or instruments (e.g., ablation tools) which may pass from the first end 24 of the multi-linked device 10 to the second end 26 of the multi-linked device 10.

The intermediate link 32 also defines a passage 76 extending from the first end 58 to the second end 60 along the longitudinal axis 62 as shown in FIG. 4B. The passage 76 may be of a size sufficient to allow one or more cables to pass therethrough. According to various embodiments, the passage 76 may be of a size sufficient to allow a tensioning cable to pass therethrough. According to various embodiments, the passage 76 is generally configured as a complex shape that comprises a combination of a first segmented hemisphere 78 that extends from the first end 58 toward the second end 60, a second segmented hemisphere 80 that extends from the first segmented hemisphere 78 toward the second end 60, a cylinder 82 that extends from the second segmented hemisphere 80 toward the second end 60, and a third segmented hemisphere 84 that extends from the cylinder 82 to the second end 60 of the intermediate link 32. According to various embodiments, the first segmented hemisphere 78 represents a portion of a sphere having a diameter on the order of approximately 4.75 millimeters, the second segmented hemisphere 80 represents a portion of a sphere having a diameter on the order of approximately 2.25 millimeters, the cylinder 82 may have a diameter on the order of approximately 1.0 millimeter, and the third segmented hemisphere 84 represents a portion of a sphere having a diameter on the order of approximately 2.25 millimeters. Other sizes are possible.

The first segmented hemisphere 78 of the passage 76 is configured to receive the second end 36 of the first link 28 when the first link 28 is coupled to the intermediate link 32.

Similarly, for a given intermediate link 32, the first segmented hemisphere 78 of the passage 76 is configured to receive the second end 60 of another intermediate link 32 when the other intermediate link 32 is coupled to the given intermediate link 32. The third segmented hemisphere 84 may serve to reduce the pinching or binding a cable when one intermediate link 32 moves relative to an adjacent intermediate link 32 coupled thereto. Similarly, when the second link 30 is coupled to a given intermediate link 32, the third segmented hemisphere 84 may serve to reduce the pinching or binding of a cable when the second link 30 moves relative to the given intermediate link 32.

With the above described structure, the first link 28 may be coupled to the intermediate link 32 by seating the second end 36 of the first link 28 in the first segmented hemisphere 78 of the passage 76 of the intermediate link 32. As the convex configuration of the second end 36 of the first link 28 generally corresponds with the concave configuration of the first segmented hemisphere 78 of the passage 76 of the intermediate link 32, the first link 28 may be coupled to the intermediate link 32 such that the longitudinal axis 38 and the first, second and third grooves 46, 48, 50 of the first link 28 are respectively aligned with the longitudinal axis 62 and the first, second and third grooves 70, 72, 74 of the intermediate link 32. The intermediate link 32 may be moved relative to the first link 28 such that the longitudinal axis 62 of the intermediate link 32 is not aligned with the longitudinal axis 38 of the first link 28. According to various embodiments, the configuration of the first link 28 and the intermediate link 32 allows for the intermediate link 32 to be moved relative to the first link 28 coupled thereto such that the longitudinal axis 38 of the first link 28 and the longitudinal axis 62 of the intermediate link 32 are up to approximately 25° out of alignment with one another. Similarly, one intermediate link 32 may be coupled to another intermediate link 32, and so on, by seating the second end 60 of one intermediate link 32 in the first segmented hemisphere 78 of the passage 76 of another intermediate link 32. As the convex configuration of the second end 60 of the intermediate link 32 generally corresponds with the concave configuration of the first segmented hemisphere 78 of the passage 76 of the intermediate link 32, the intermediate links 32 may be coupled such that the respective longitudinal axes 62 and the respective first, second and third grooves 46, 48, 50 of the intermediate links 32 are aligned. The coupled intermediate links 32 may be moved relative to one another such that the respective longitudinal axes 62 of the coupled intermediate links 32 are not aligned. According to various embodiments, the configuration of the coupled intermediate links 32 allows for one intermediate link 32 to be moved relative to an adjacent intermediate link 32 coupled thereto such that the respective longitudinal axes 62 are up to approximately 25° out of alignment with one another.

Figure 5A:
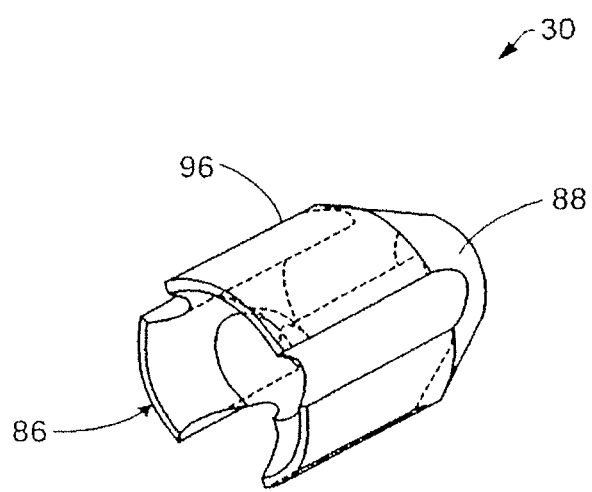
FIGS. 5A-5C illustrate various embodiments of a distal link of the core mechanism.
Figure 5B:
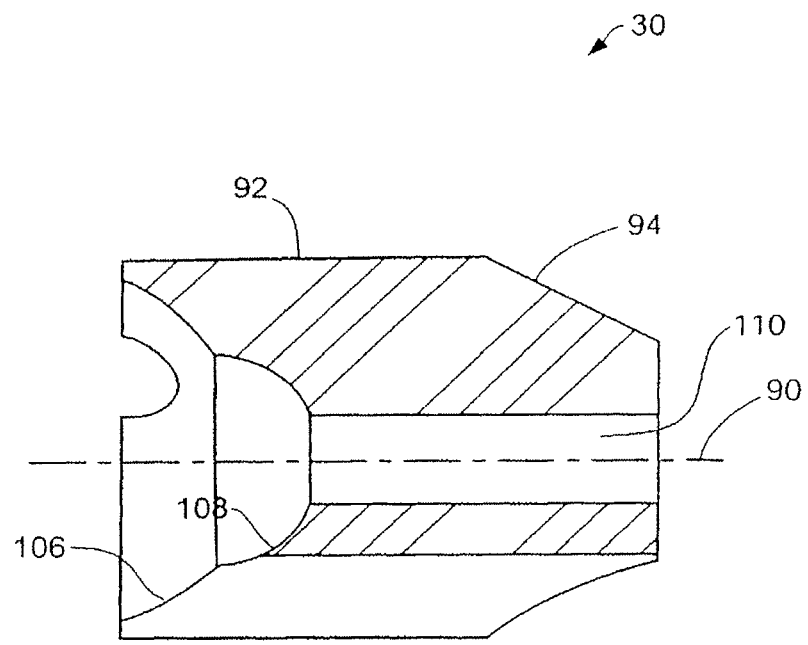
Figure 5C:
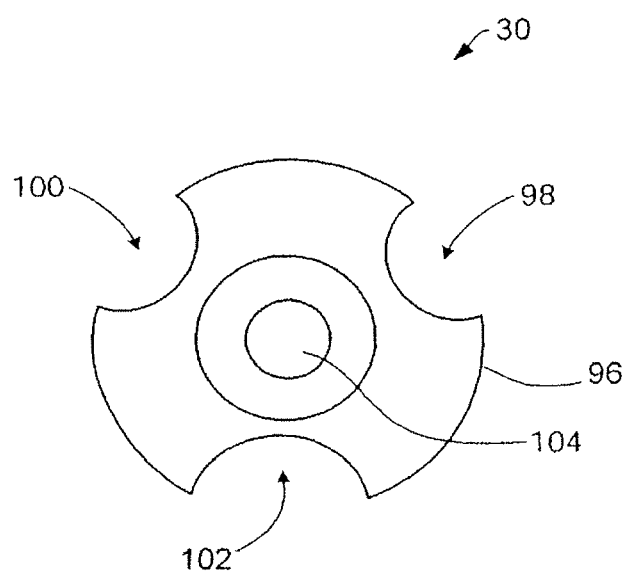

FIGS. 5A-5C illustrate various embodiments of the second link 30 (inner distal link) of the first mechanism 12. The second link 30 includes a first end 86 and a second end 88, and defines a longitudinal axis 90 that passes through the center of the first end 86 and the center of the second end 88 as shown in FIG. 5B. The second link 30 may be fabricated from any suitable material. According to various embodiments, the second link 30 is fabricated from a thermoplastic material such as, for example, Delrin®.

The second link 30 comprises a first portion 92 and a second portion 94. The first portion 92 may be considered the proximal portion and the second portion 94 may be considered the distal portion. The first portion 92 may be fabricated integral with the second portion 94. The first portion 92 has a generally cylindrical shaped exterior, and extends from the first end 86 of the second link 30 toward the second end 88 of the second link 30. According to various embodiments, the second portion 94 has a generally cylindrically shaped exterior where it contacts the first portion 92, and tapers toward the second end 88 of the second link 30. The exterior of the second portion 64 is configured in the form of a generally segmented cone. According to various embodiments, the diameter of the second link 30 may be on the order of approximately 4.75 millimeters at the first end 86 thereof, and the taper of the second portion 94 may be at an angle of approximately 30° relative to the exterior of the first portion 92. The length of the second link 30 may be on the order of approximately 5.90 millimeters. However, one skilled in the art will appreciate that the length or diameter of the second link 30 can vary based on the application.

The second link 30 also comprises a first surface 96 that extends from the first end 86 of the second link 30 to the second end 88 of the second link 30. The first surface 96 may be considered the outer surface of the second link 30. The second link 30 also defines a first groove 98 parallel to the longitudinal axis 90 along the first surface 96, a second groove 100 parallel to the longitudinal axis 90 along the first surface 96, and a third groove 102 parallel to the longitudinal axis 90 along the first surface 96. Each of the first, second and third grooves 98, 100, 102 extend along the first surface 96 from the first end 86 of the second link 30 toward the second end 88 of the second link 30. The first, second and third grooves 98, 100, 102 may be semi-tubular shaped and may be evenly spaced about the first surface 96 of the second link 30 as shown in FIG. 5C. According to various embodiments, the first, second, and third grooves 98, 100, 102 may be configured in the shape of a segmented cylinder. The size of each of the grooves 98, 100, 102 may be identical to one another or may be different from one another. For example, according to various embodiments, the first and second grooves 98, 100 are configured as segments of a cylinder having a diameter on the order of approximately 1.25 millimeters at the first end 86 of the second link 30, and the third groove 102 is configured as a segment of a cylinder having a diameter on the order of approximately 2.50 millimeters at the first end 86 of the second link 30. The first, second and third grooves 98, 100, 102 are each configured to receive and partially surround any of a variety of tools or instruments (e.g., ablation tools) which may pass from the first end 24 of the multi-linked device 10 to the second end 26 of the multi-linked device 10.

The second link 30 also defines a passage 104 extending from the first end 86 to the second end 88 along the longitudinal axis 90 as shown in FIG. 5B. The passage 104 may be of a size sufficient to allow at least one cable to pass therethrough. According to various embodiments, the passage 104 may be of a size sufficient to allow a tensioning cable to pass therethrough. According to various embodiments, the passage 104 is generally configured as a complex shape that comprises a combination of a first segmented hemisphere 106 that extends from the first end 86 toward the second end 88, a second segmented hemisphere 108 that extends from the first segmented hemisphere 106 toward the second end 88, and a cylinder 110 that extends from the second segmented hemisphere 108 to the second end 88 of the second link 30. According to various embodiments, the first segmented hemisphere 106 represents a portion of a sphere having a diameter on the order of approximately 4.75 millimeters, the second segmented hemisphere 108 represents a portion of a sphere having a diameter on the order of approximately 2.50 millimeters, and the cylinder 110 may have a diameter on the order of approximately 1.0 millimeter. The first segmented hemisphere 106 of the passage 104 may be configured to receive the second end 60 of an intermediate link 32 when the intermediate link 32 is coupled to the second link 30.

With the above described structure, an intermediate link 32 may be coupled to the second link 30 by seating the second end 60 of the intermediate link 32 in the first segmented hemisphere 106 of the passage 104 of the second link 30. As the convex configuration of the second end 60 of the intermediate link 32 generally corresponds with the concave configuration of the first segmented hemisphere 106 of the passage 104 of the second link 30, the intermediate link 32 may be coupled to the second link 30 such that the longitudinal axis 62 and the first, second and third grooves 70, 72, 74 of the intermediate link 32 are respectively aligned with the longitudinal axis 90 and the first, second and third grooves 98, 100, 102 of the second link 30. The second link 30 may be moved relative to the intermediate link 32 coupled thereto such that the respective longitudinal axes 62, 90 are not aligned. According to various embodiments, the configuration of the second link 30 allows for an intermediate link 32 coupled thereto to be moved relative to the second link 30 such that the respective longitudinal axes 62, 90 are up to approximately 25° out of alignment with one another.

Figure 6:
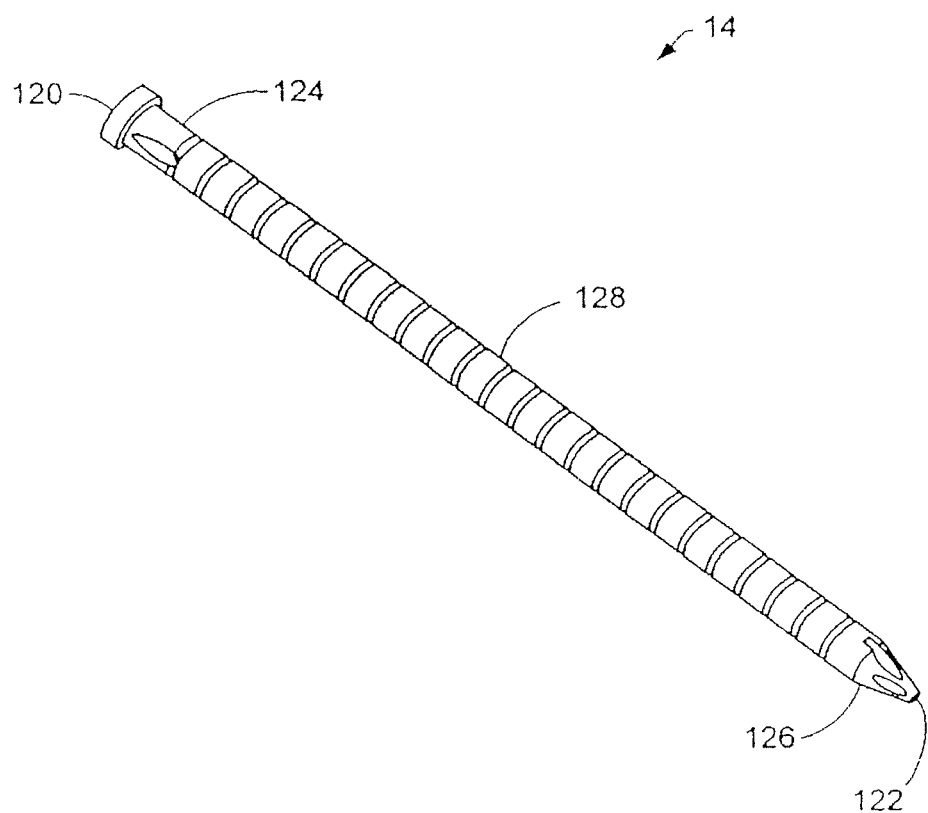
FIG. 6 illustrates various embodiments of a sleeve mechanism of the device of FIG. 1.

FIG. 6 illustrates various embodiments of the second mechanism 14 of the device 10. The second mechanism 14 is a multi-linked mechanism and includes a first end 120 and a second end 122. The first end 120 may be considered the proximal end and the second end 122 may be considered the distal end. The second mechanism 14 comprises a first link 124, a second link 126, and any number of intermediate links 128 between the first and second links 124, 126. The first link 124 may be considered the proximal link, and the second link 126 may be considered the distal link.

Figure 7A:
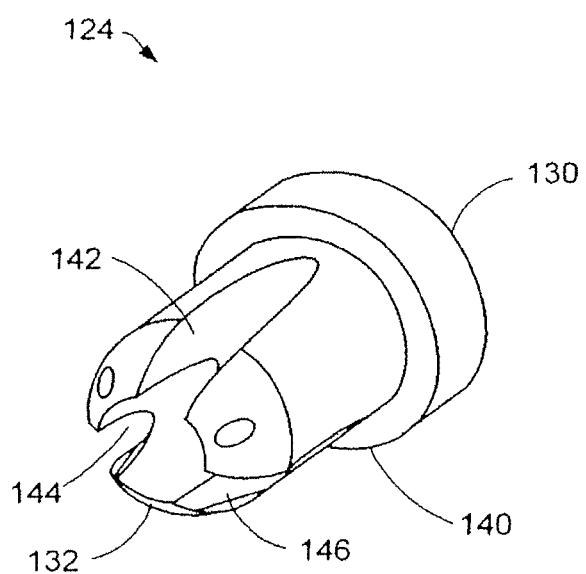
FIGS. 7A-7C illustrate various embodiments of a proximal link of the sleeve mechanism.
Figure 7B:
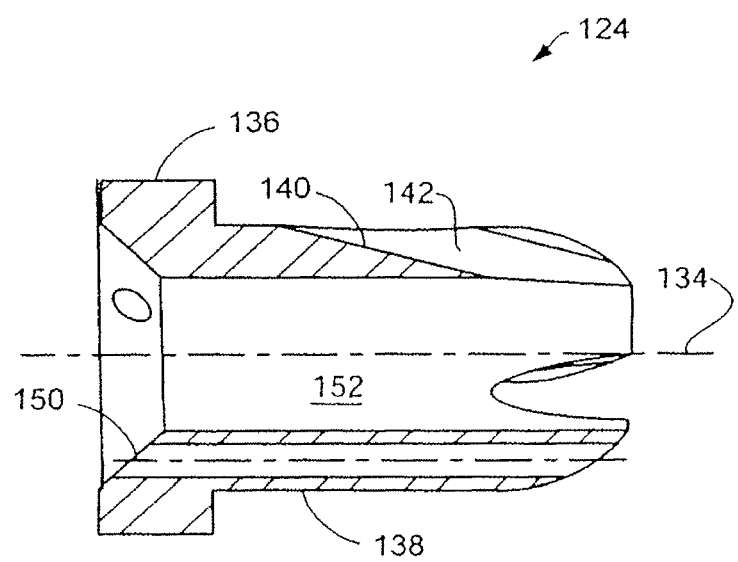
Figure 7C:
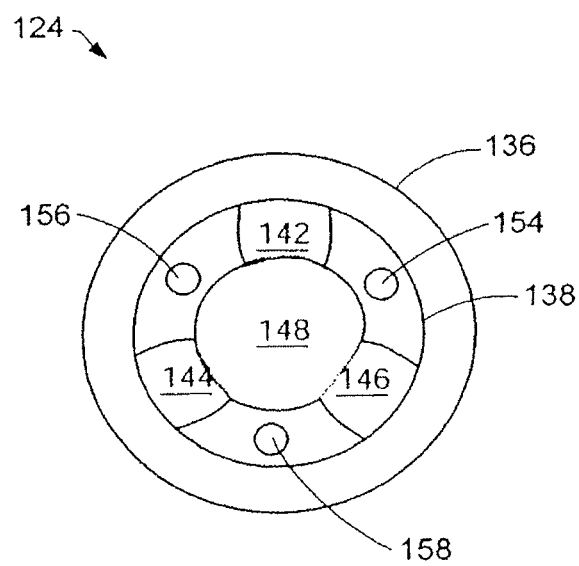

FIGS. 7A-7C illustrate various embodiments of the first link 124 (outer proximal link) of the second mechanism 14. The first link 124 includes a first end 130 and a second end 132, and defines a longitudinal axis 134 that passes through the center of the first end 130 and the center of the second end 132 as shown in FIG. 7B. The first link 124 may be fabricated from any suitable material. According to various embodiments, the first link 124 is fabricated from a stainless steel material such as, for example, 316 stainless steel. The first link 124 has a generally bullet-shaped exterior and is described in more detail hereinbelow.

The first link 124 comprises a first portion 136 and a second portion 138. The first portion 136 may be considered the proximal portion and the second portion 138 may be considered the distal portion. The first portion 136 may be fabricated integral with the second portion 138. The first portion 136 has a cylindrical shaped exterior, and extends from the first end 130 of the first link 124 toward the second end 132 of the first link 124. According to various embodiments, the diameter of the first portion 136 may be on the order of approximately 12.70 millimeters. Other sizes are possible.

The second portion 138 has a generally cylindrically shaped exterior. The second portion 138 has a cylindrically shaped exterior where it contacts the first portion 136, and tapers toward the second end 132 of the first link 124. The second portion 138 may be shaped in the form of a generally segmented hemisphere at the second end 132 of the first link 124. According to various embodiments, the diameter of the second portion 138 may be on the order of approximately 9.50 millimeters where it contacts the first portion 136. Other sizes and shapes are possible.

The second portion 138 comprises a first surface 140. The first surface 140 may be considered the outer surface of the second portion 138. The second portion 138 defines a first groove 142 along the first surface 140, a second groove 144 along the first surface 140, and a third groove 146 along the first surface 140. Each of the first, second and third grooves 142, 144, 146 are oblique relative to the longitudinal axis 134 and extend along the first surface 140 toward the second end 132 of the first link 124. According to various embodiments, each of the grooves 142, 144, 146 are oriented at an angle on the order of approximately 15° relative to the longitudinal axis 134. As shown in FIG. 7C, the first, second and third grooves 142, 144, 146 may be evenly spaced about the first surface 140 of the first link 124. According to various embodiments, the first, second, and third grooves 142, 144, 146 may be configured in the shape of a segmented cylinder. The size of each of the grooves 142, 144, 146 may identical to one another or may be different from one another. For example, according to various embodiments, each of the grooves 142, 144, 146 are configured as segments of respective cylinders having diameters on the order of approximately 3.0 millimeters. The first, second and third grooves 142, 144, 146 are each configured to facilitate the introduction of various tools or instruments (e.g., ablation tools) into the multi-linked device 10. The length of the first link 124 may be on the order of approximately 18.5 millimeters. However, one skilled in the art will appreciate that the length or diameter of the first link 124 can vary based on the application.

The first link 124 also defines a passage 148 extending from the first end 130 to the second end 132 along the longitudinal axis 134 as shown in FIG. 7B. The passage 148 is of a size sufficient to allow the first mechanism 12 to pass therethrough. According to various embodiments, the passage 148 is generally configured as a complex shape that comprises a combination of a segmented cone 150 that extends from the first end 130 toward the second end 132, and a cylinder 152 that extends from the segmented cone 150 to the second end 132 of the first link 124. According to various embodiments, the segmented cone 150 has a diameter on the order of approximately 7.0 millimeters at the first end 130 of the first link 124, and may be tapered at an angle on the order of approximately 45° relative to the longitudinal axis 134. The cylinder 152 may have a diameter on the order of approximately 5.50 millimeters. Other dimensions are possible.

The first link 124 also defines a first through-hole 154, a second through-hole 156, and a third through-hole 158. (See FIG. 7C). The first through-hole 154 is substantially parallel to the longitudinal axis 134, extends from the first portion 136 toward the second end 132, and is positioned between the passage 148 and the first surface 140. The second through-hole 156 is substantially parallel to the longitudinal axis 134, extends from the first portion 136 to the second end 132, and is positioned between the passage 148 and the first surface 140. The third through-hole 158 is substantially parallel to the longitudinal axis 134, extends from the first portion 136 to the second end 132, and is positioned between the passage 148 and the first surface 140. The first, second and third through-holes 154, 156, 158 are generally cylindrically shaped. According to various embodiments, the through-holes 154, 156, 158 are evenly spaced from one another as shown in FIG. 7C. The size of each of the through-holes 154, 156, 158 may be identical to one another or may be different from one another. For example, according to various embodiments, the respective diameters associated with the through-holes 154, 156, 158 may each be on the order of approximately 1.20 millimeters. The first through-hole 154 is configured to receive and surround a cable. The second through-hole 156 is configured to receive and surround a cable. The third through-hole 158 is configured to receive and surround a cable. The first, second and third through-holes 154, 156, 158 may serve as guidepaths for movement of the cables.

Figure 8A:
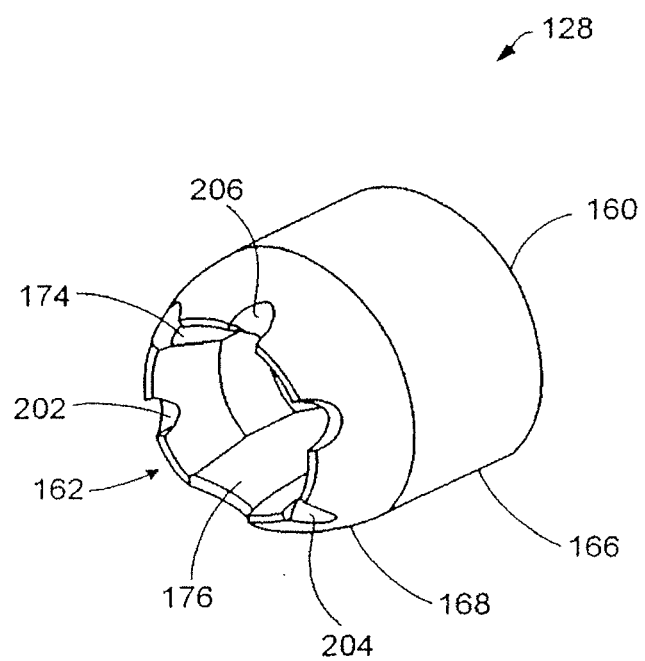
FIGS. 8A-8C illustrate various embodiments of an intermediate link of the sleeve mechanism.
Figure 8B:
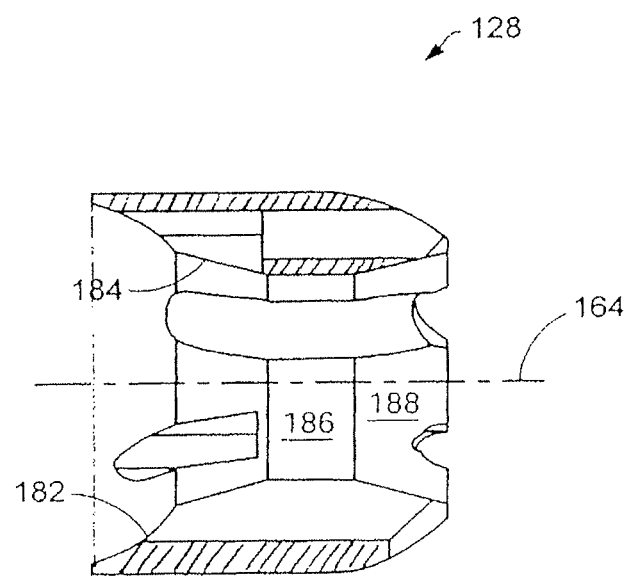
Figure 8C:
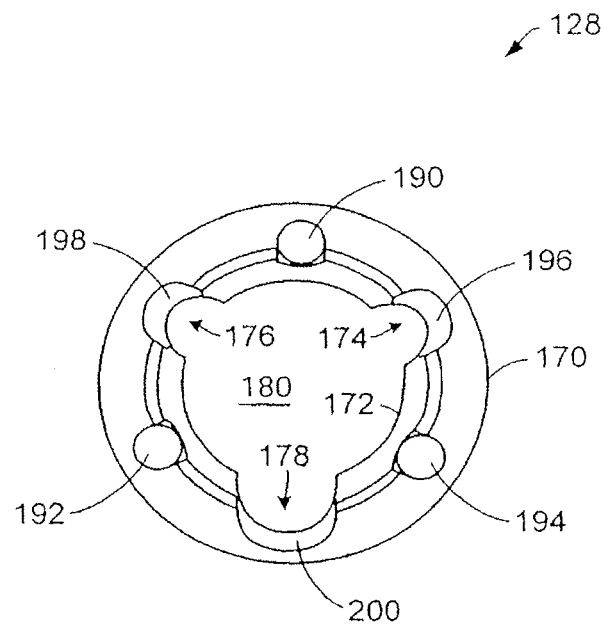

FIGS. 8A-8C illustrate various embodiments of one of the intermediate links 128 (outer intermediate link) of the second mechanism 14. The intermediate link 128 is representative of the other intermediate links 128. The intermediate link 128 includes a first end 160 and a second end 162, and defines a longitudinal axis 164 that passes through the center of the first end 160 and the center of the second end 162 as shown in FIG. 8C. The intermediate link 128 may be fabricated from any suitable material. According to various embodiments, the intermediate link 128 is fabricated from a polymer thermosplastic material such as, for example, polysulfone. The intermediate link 128 has a generally bullet-shaped exterior and is described in more detail hereinbelow.

The intermediate link 128 comprises a first portion 166 and a second portion 168. The first portion 166 may be considered the proximal portion and the second portion 168 may be considered the distal portion. The first portion 166 may be fabricated integral with the second portion 168. The first portion 166 has a generally cylindrical shaped exterior, and extends from the first end 160 of the intermediate link 128 toward the second end 162 of the intermediate link 128. According to various embodiments, the second portion 168 has a generally cylindrically shaped exterior where it contacts the first portion 166, and tapers toward the second end 162 of the intermediate link 128. The exterior of the second portion 168 is configured in the form of a generally segmented hemisphere. According to various embodiments, the diameter of the intermediate link 128 is on the order of approximately 9.65 millimeters at the first end 160 thereof. The length of the intermediate link 128 may be on the order of approximately 8.40 millimeters. However, one skilled in the art will appreciate that the dimensions of the intermediate link 128 can vary based on the application.

The intermediate link 128 also comprises a first surface 170 that extends from the first end 160 of the intermediate link 128 to the second end 162 of the intermediate link 128, and a second surface 172 that extends from the first end 160 of the intermediate link 128 to the second end 162 of the intermediate link 128. The first surface 170 may be considered the outer surface of the intermediate link 128, and the second surface 172 may be considered the inner surface of the intermediate link 128. The intermediate link 32 also defines a first groove 174 substantially parallel to the longitudinal axis 164 along the second surface 172, a second groove 176 substantially parallel to the longitudinal axis 164 along the second surface 172, and a third groove 178 substantially parallel to the longitudinal axis 164 along the second surface 172. Each of the first, second and third grooves 174, 176, 178 extend along the second surface 172 toward the second end 162 of the intermediate link 128. The first, second and third grooves 174, 176, 178 may be semi-tubular shaped and may be evenly spaced about the second surface 172 of the intermediate link 128 as shown in FIG. 8C. According to various embodiments, the first, second, and third grooves 174, 176, 178 may be configured in the shape of a segmented cylinder. The size of each of the grooves 174, 176, 178 may be identical to one another or may be different from one another. For example, according to various embodiments, the first and second grooves 174, 176 are configured as segments of cylinders having diameters on the order of approximately 1.75 millimeters at the first end 160 of the intermediate link 128, and the third groove 178 is configured as a segment of a cylinder having a diameter on the order of approximately 2.50 millimeters at the first end 160 of the intermediate link 128. The first, second and third grooves 174, 176, 178 are each configured to receive and partially surround any of a variety of tools or instruments (e.g., ablation tools) which may pass from the first end 24 of the multi-linked device 10 to the second end 26 of the multi-linked device 10.

The intermediate link 128 also defines a passage 180 extending from the first end 160 to the second end 162 along the longitudinal axis 164 as shown in FIG. 8B. The passage 180 is of a size sufficient to allow the first mechanism 12 to pass therethrough. According to various embodiments, the passage 180 is generally configured as a complex shape that comprises a combination of a segmented hemisphere 182 that extends from the first end 160 toward the second end 162, a first segmented cone 184 that extends from the segmented hemisphere 182 toward the second end 162, a cylinder 186 that extends from the first segmented cone 184 toward the second end 162, and a second segmented cone 188 that extends from the cylinder 186 to the second end 162 of the intermediate link 128. According to various embodiments, the segmented hemisphere 182 represents a portion of a sphere having a diameter on the order of approximately 9.65 millimeters, the first segmented cone 184 is tapered at an angle on the order of approximately 15° relative to the longitudinal axis 164, the cylinder 186 has a diameter on the order of approximately 5.50 millimeters, and the second segmented cone 188 is tapered at an angle on the order of approximately 15° relative to the longitudinal axis 164. The segmented hemisphere 182 of the passage 180 is configured to receive the second end 132 of the first link 124 when the first link 124 is coupled to the intermediate link 128. Similarly, for a given intermediate link 128, the segmented hemisphere 182 of the passage 180 is configured to receive the second end 162 of another intermediate link 128 when the other intermediate link 128 is coupled to the given intermediate link 128.

The intermediate link 128 also defines a first through-hole 190, a second through-hole 192, and a third through-hole 194. (See FIG. 8C). The first through-hole 190 is substantially parallel to the longitudinal axis 164, extends from the first portion 166 toward the second end 162, and is positioned between the passage 180 and the first surface 170. The second through-hole 192 is substantially parallel to the longitudinal axis 164, extends from the first portion 166 to the second end 162, and is positioned between the passage 180 and the first surface 170. The third through-hole 194 is substantially parallel to the longitudinal axis 164, extends from the first portion 166 to the second end 162, and is positioned between the passage 180 and the first surface 170. The first, second and third through-holes 190, 192, 194 are generally cylindrically shaped. According to various embodiments, the through-holes 190, 192, 194 are evenly spaced from one another. The size of each of the through-holes 190, 192, 194 may be identical to one another or may be different from one another. For example, according to various embodiments, the respective diameters associated with the through-holes 190, 192, 194 may each be on the order of approximately 1.25 millimeters. The first through-hole 190 is configured to receive and surround a cable. The second through-hole 192 is configured to receive and surround a cable. The third through-hole 194 is configured to receive and surround a cable. The first, second and third through-holes 190, 192, 194 may serve as guidepaths for movement of the cables.

As shown in FIG. 8C, the intermediate link 128 also defines first, second and third indents 196, 198, 200 at the second end 162 thereof resulting, in part, from the combination of the taper associated with the second portion 168 and the configuration and orientation of the first, second, and third grooves 174, 176, 178. The first, second and third indents 196, 198, 200 may be evenly spaced about the second end 162 of the intermediate link 128 as shown in FIG. 8C. The first, second and third indents 196, 198, 200 may serve to reduce the pinching or binding of various tools or instruments (e.g., ablation tools) when one intermediate link 128 of the second mechanism 14 is moved relative to another intermediate link 128 coupled thereto.

The intermediate link 128 also defines fourth, fifth and sixth indents 202, 204, 206 at the second end 162 thereof resulting from the combination of the taper associated with the second portion 168 and the configuration and orientation of the first, second, and third through-holes 190, 192, 194. The fourth, fifth and sixth indents 202, 204, 206 may be evenly spaced about the second end 162 of the intermediate link 128, and may be evenly spaced from the first, second and third indents 196, 198, 200 as shown in FIG. 8C. The fourth, fifth and sixth indents 202, 204, 206 may serve to reduce the pinching or binding of the cables when one intermediate link 128 of the second mechanism 14 is moved relative to another intermediate link 128 coupled thereto.

According to various embodiments, an intermediate link 128 may also define an opening (not shown) that extends from the second surface 172 or from one of the grooves 174, 176, 178 to the first surface 170 of the intermediate link 128. The intermediate link 128 may have any number of such openings, and any number of the intermediate links 128 may have such openings. Referring to FIGS. 2 and 4, the opening may be utilized as an exit point for a tool or instrument which may pass from the first end 24 of the multi-linked device 10 toward the second end 26 of the multi-linked device 10. For such embodiments, the respective intermediate link 128 may be positioned proximate to the second link 126 of the second mechanism 14. The opening may be oriented at any angle relative to the longitudinal axis 134 of the intermediate link 128. When the first mechanism 12 is removed from the second mechanism 14, and a relatively large tool or instrument is advanced from the first end 120 of the second mechanism 14 to the second end 122 of the second mechanism 14, sufficient room may not exist for a second tool or instrument (e.g., fiber optic cable) to pass through the second end 122 of the second mechanism 14. For such instances, the second tool or instrument may exit through an opening of one of the intermediate links 128.

With the above described structure, the first link 124 may be coupled to the intermediate link 128 by seating the second end 132 of the first link 124 in the segmented hemisphere 182 of the passage 180 of the intermediate link 128. As the convex configuration of the second end 132 of the first link 124 generally corresponds with the concave configuration of the segmented hemisphere 182 of the passage 180 of the intermediate link 128, the first link 124 may be coupled to the intermediate link 128 such that the longitudinal axis 134, the first, second and third grooves 142, 144, 146, and the first, second and third through-holes 154, 156, 158 of the first link 124 are respectively aligned with the longitudinal axis 164, the first, second and third grooves 174, 176, 178, and the first, second and third through-holes 190, 192, 194 of the intermediate link 128. The intermediate link 128 may be moved relative to the first link 124 such that the longitudinal axis 164 of the intermediate link 128 is not aligned with the longitudinal axis 134 of the first link 124. According to various embodiments, the configuration of the first link 124 and the intermediate link 128 allows for the intermediate link 128 to be moved relative to the first link 124 coupled thereto such that the longitudinal axis 134 of the first link 124 and the longitudinal axis 164 of the intermediate link 128 are up to approximately 10° out of alignment with one another. Similarly, one intermediate link 128 may be coupled to another intermediate link 128, and so on, by seating the second end 162 of one intermediate link 128 in the segmented hemisphere 182 of the passage 180 of another intermediate link 128. As the convex configuration of the second end 162 of the intermediate link 128 generally corresponds with the concave configuration of the segmented hemisphere 182 of the passage 180 of the intermediate link 128, the intermediate links 128 may be coupled such that the respective longitudinal axes 164, the respective first, second and third grooves 174, 176, 178, and the respective first, second and third through-holes 190, 192, 194 of the intermediate links 128 are aligned. The coupled intermediate links 128 may be moved relative to one another such that the respective longitudinal axes 164 of the coupled intermediate links 128 are not aligned. According to various embodiments, the configuration of the coupled intermediate links 128 allows for one intermediate link 128 to be moved relative to another intermediate link 128 coupled thereto such that the respective longitudinal axes 164 are up to approximately 10° out of alignment with one another.

Figure 9A:
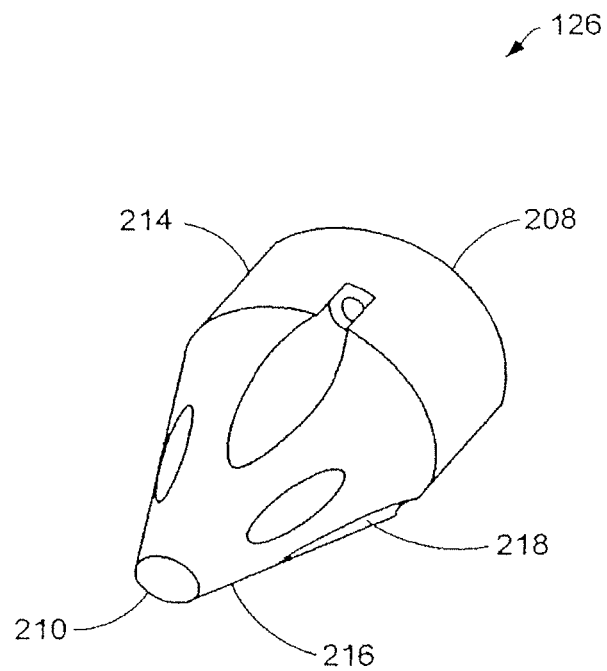
FIGS. 9A-9D illustrate various embodiments of a distal link of the sleeve mechanism.
Figure 9B:
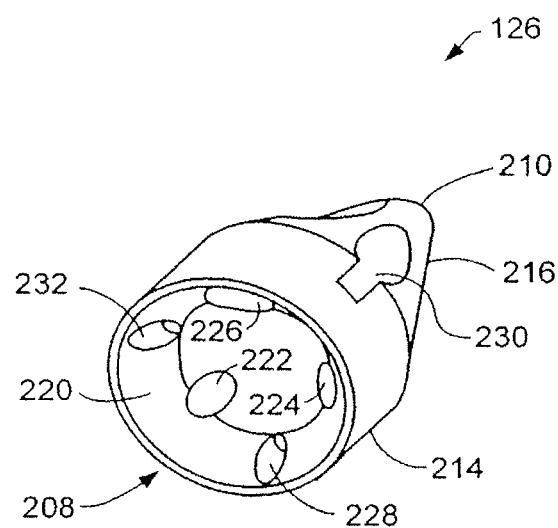
Figure 9C:
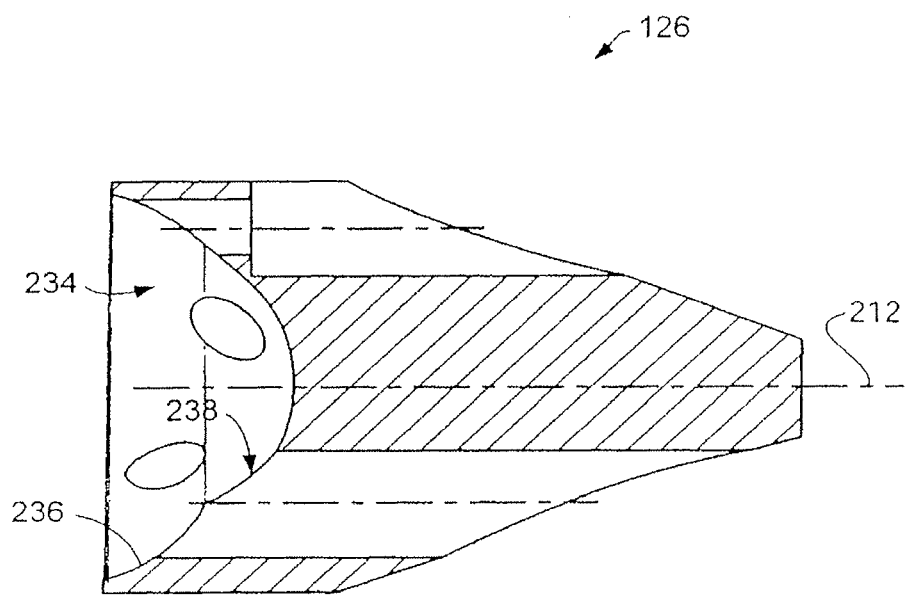

FIGS. 9A-9D illustrate various embodiments of the second link 126 (outer distal link) of the second mechanism 14. The second link 126 includes a first end 208 and a second end 210, and defines a longitudinal axis 212 that passes through the center of the first end 208 and the center of the second end 210 as shown in FIG. 9C. The second link 126 may be fabricated from any suitable material. According to various embodiments, the second link 126 is fabricated from a thermoplastic material such as, for example, Delrin®.

The second link 126 comprises a first portion 214 and a second portion 216. The first portion 214 may be considered the proximal portion and the second portion 216 may be considered the distal portion. The first portion 214 may be fabricated integral with the second portion 216. The first portion 214 has a generally cylindrical shaped exterior, and extends from the first end 208 of the second link 126 toward the second end 210 of the second link 126. According to various embodiments, the diameter of the first portion 214 is on the order of approximately 4.80 millimeters.

According to various embodiments, the second portion 216 has a generally cylindrically shaped exterior where it contacts the first portion 214, and tapers toward the second end 210 of the second link 126. The exterior of the second portion 216 is configured in the form of a generally segmented cone. According to various embodiments, the exterior of the second portion 216 tapers from the first portion 214 to the second end 210 of the second link 126 at an angle on the order of approximately 20° relative to the exterior of the first portion 214. The length of the second link 126 may be on the order of approximately 15 millimeters. However, one skilled in the art will appreciate that the length of the second link 126 can vary based on the application.

The second link 126 also comprises a first surface 218 that extends from the first end 208 of the second link 126 to the second end 210 of the second link 126, and a second surface 220 that extends from the first end 208 of the second link 126 toward the second end 210 of the second link 126. The first surface 218 may be considered the outer surface of the second link 126, and the second surface 220 may be considered the inner surface of the second link 126.

Figure 9D:
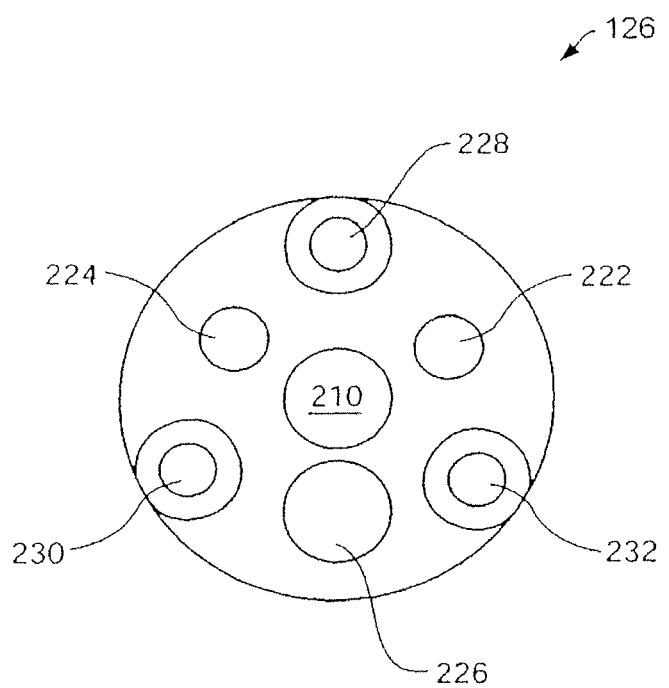

The second link 126 also defines a first port 222, a second port 224, and a third port 226. (See FIG. 9B). The first port 222 extends from the second surface 220 to the first surface 218 and is substantially parallel to the longitudinal axis 212. The second port 224 extends from the second surface 220 to the first surface 218 and is substantially parallel to the longitudinal axis 212. The third port 226 extends from the second surface 220 to the first surface 218 and is substantially parallel to the longitudinal axis 212. The first, second and third ports 222, 224, 226 may be cylindrical shaped and may be evenly spaced about the longitudinal axis 212 of the second link 126 as shown in FIG. 9D. The size of each of the ports 222, 224, 226 may be identical to one another or may be different from one another. For example, according to various embodiments, the first and second ports 222, 224 are configured as cylinders having diameters on the order of approximately 1.50 millimeters, and the third port 226 is configured as a cylinder having a diameter on the order of approximately 2.50 millimeters. Other dimensions are possible. The first, second and third ports 222, 224, 226 are each configured to receive and surround any of a variety of tools or instruments (e.g., ablation tools) which may pass from the first end 24 of the multi-linked device 10 to the second end 26 of the multi-linked device 10.

The second link 126 also defines a first through-hole 228, a second through-hole 230, and a third through-hole 232. (See FIG. 9B). The first through-hole 228 extends from the second surface 220 to the first surface 218 and is substantially parallel to the longitudinal axis 212. The second through-hole 230 extends from the second surface 220 to the first surface 218 and is substantially parallel to the longitudinal axis 212. The third through-hole 232 extends from the second surface 220 to the first surface 218 and is substantially parallel to the longitudinal axis 212. The first, second and third through-holes 228, 230, 232 are generally cylindrically shaped. According to various embodiments, the through-holes 228, 230, 232 are evenly spaced from one another as shown in FIG. 9D. The size of each of the through-holes 228, 230, 232 may be identical to one another or may be different from one another. For example, according to various embodiments, the respective diameters associated with the through-holes 228, 230, 232 may each be on the order of approximately 1.25 millimeters. The first through-hole 228 is configured to receive and surround a cable. The second through-hole 230 is configured to receive and surround a cable. The third through-hole 232 is configured to receive and surround a cable.

The second link 126 also defines a recess 234 that extends from the first end 208 toward the second end 210 along the longitudinal axis 212 as shown in FIG. 9C. According to various embodiments, the recess 234 is generally configured as a complex shape that comprises a combination of a first segmented hemisphere 236 that extends from the first end 208 toward the second end 210, and a second segmented hemisphere 238 that extends from the first segmented hemisphere 236 toward the second end 210 of the second link 126. According to various embodiments, the first segmented hemisphere 236 represents a portion of a sphere having a diameter on the order of approximately 9.50 millimeters, and the second segmented hemisphere 238 represents a portion of a sphere having a diameter on the order of approximately 7.0 millimeters. The first segmented hemisphere 236 of the recess 234 is configured to receive the second end 162 of an intermediate link 128 when the intermediate link 128 is coupled to the second link 126.

With the above described structure, an intermediate link 128 may be coupled to the second link 126 by seating the second end 162 of the intermediate link 128 in the first segmented hemisphere 236 of the recess 234 of the second link 126. As the convex configuration of the second end 162 of the intermediate link 128 generally corresponds with the concave configuration of the first segmented hemisphere 236 of the recess 234 of the second link 126, the intermediate link 128 may be coupled to the second link 126 such that the longitudinal axis 164, the first, second and third grooves 174, 176, 178, and the first, second and third through-holes 190, 192, 194 of the intermediate link 128 are respectively aligned with the longitudinal axis 212, the first, second and third ports 222, 224, 226, and the first, second and third through-holes 228, 230, 232 of the second link 126. The second link 126 may be moved relative to the intermediate link 128 coupled thereto such that the respective longitudinal axes 164, 212 are not aligned. According to various embodiments, the configuration of the second link 126 allows for an intermediate link 128 coupled thereto to be moved relative to the second link 126 such that the respective longitudinal axes 164, 212 are up to approximately 10° out of alignment with one another.

When the first mechanism 12 is inserted into the second mechanism 14, the first second and third grooves 70, 72, 74 of the intermediate links 32 of the first mechanism 12 may be substantially aligned with the first, second and third grooves 174, 176, 178 of the intermediate links 128 of the second mechanism 14, and the first, second and third grooves 98, 100, 102 of the second link 30 of the first mechanism 12 may be substantially aligned with the first, second and third ports 222, 224, 226 of the second link 126 of the second mechanism 14. The combination of the first grooves 70 of the intermediate links 32 of the first mechanism 12 aligned with the first grooves 174 of the intermediate links 128 of the second mechanism 14 allows the respective first grooves 70, 174 to collectively serve as a first working port that is substantially aligned with the first port 222 of the second link 126 of the second mechanism 14. The first groove 70 may be considered the inner portion of the first working port and the first groove 174 may be considered the outer portion of the first working port.

Similarly, the combination of the second grooves 72 of the intermediate links 32 of the first mechanism 12 aligned with the second grooves 176 of the intermediate links 128 of the second mechanism 14 allows the respective second grooves 72, 176 to collectively serve as a second working port that is substantially aligned with the second port 224 of the second link 126 of the second mechanism 14, and the combination of the third grooves 74 of the intermediate links 32 of the first mechanism 12 aligned with the third grooves 178 of the intermediate links 128 of the second mechanism 14 allows the respective third grooves 74, 178 to collectively serve as a third working port that is substantially aligned with the third port 226 of the second link 126 of the second mechanism 14. The second groove 72 may be considered the inner portion of the second working port and the second groove 176 may be considered the outer portion of the second working port. The third groove 74 may be considered the inner portion of the third working port and the third groove 178 may be considered the outer portion of the third working port. The first, second and third working ports may be utilized to pass various tools or instruments (e.g., ablation tools) from the first end 24 of the multi-linked device 10 to the second end 26 of the multi-linked device 10. For the exemplary sizes described hereinabove, the third working port is larger than the first and second working ports. Accordingly, the third working port may be utilized to carry a particular tool or instrument that is too large to be carried by the first or second working ports.

When the respective grooves 70, 72, 74, 174, 176, 178 of the respective intermediate links 32, 128 are aligned and collectively surround the various tools and instruments, the combination of the grooves 70, 72, 74, 174, 176, 178 and the tools and instruments may serve to limit or prevent the rotation of the first mechanism 12 relative to the second mechanism 14.

As the diameter of the passage 180 of the intermediate link 128 of the second mechanism 14 is larger than the diameter of any portion of the first mechanism 12, a three-dimensional space 240 exists between the first mechanism 12 and the second mechanism 14 when the first mechanism 12 is received by the second mechanism 14 (See FIG. 1B). According to various embodiments, the space 240 may be utilized to carry wiring, tools, instruments, etc. from the first end 24 of the multi-linked device 10 toward the second end 26 of the multi-linked device 10.

According to various embodiments, one or more steering cables may be fabricated from any suitable material. For example, according to various embodiments, the steering cables may be fabricated from a polyethylene fiber cable such as, for example, Spectra®. The steering cables may be utilized to control the movement of the multi-linked device 10. For example, by applying a substantially equal tension to each of the steering cables, the first mechanism 12 and/or second mechanism 14 may be steered in a direction such that the respective longitudinal axes 38, 62, 90, 134, 164, 212 of each of the links 28, 30, 32, 124, 126, 128 are all aligned. By applying a different tension to one or more of the steering cables, the first mechanism 12 and/or the second mechanism 14 may be steered in a direction such that the respective longitudinal axes 38, 62, 90, 134, 164, 212 of each of the links 28, 30, 32, 124, 126, 128 are not all aligned. The cables 16, 18, 20 may also be utilized to control the relative state of the second mechanism 14. For example, when a uniform tension is applied to the steering cables, the second mechanism 14 may be placed in a "rigid" state, and when a tension is removed from the steering cables, the second mechanism 14 may be placed in a "limp" state. According to various embodiments, one or more of the steering cables may be attached at the first end 130 of the first link 124 of the second mechanism 14 to respective pullies (not shown) by, for example, respective stopper knots. The steering cables may be attached to the second end 132 of the second link 126 of the second mechanism 14 by, for example, respective stopper knots. One skilled in the art will appreciate that, according to other embodiments, the "rigid" and "limp" states may be achieved by subjecting the first and/or second mechanisms 12, 14 to a twisting force, or by any other manner known in the art.

According to various embodiments, one or more tensioning cables may be fabricated from any suitable material. For example, according to various embodiments, the tensioning cables may be fabricated from a polyethylene fiber cable such as, for example, Spectra®. The tensioning cables may be utilized to control the relative state of the first mechanism 12. For example, when the tensioning cable is drawn tight, the first mechanism 12 may be placed in a "rigid" state, whereas when the tensioning cable is let loose, the first mechanism 12 may be placed in a "limp" state. According to various embodiments, the tensioning cable may be attached at the first end 34 of the first link 28 of the first mechanism 12 to a pulley (not shown) by, for example, a stopper knot. The tensioning cable may be attached to the second end 88 of the second link 30 of the first mechanism 12 by, for example, a stopper knot.

Figure 10:
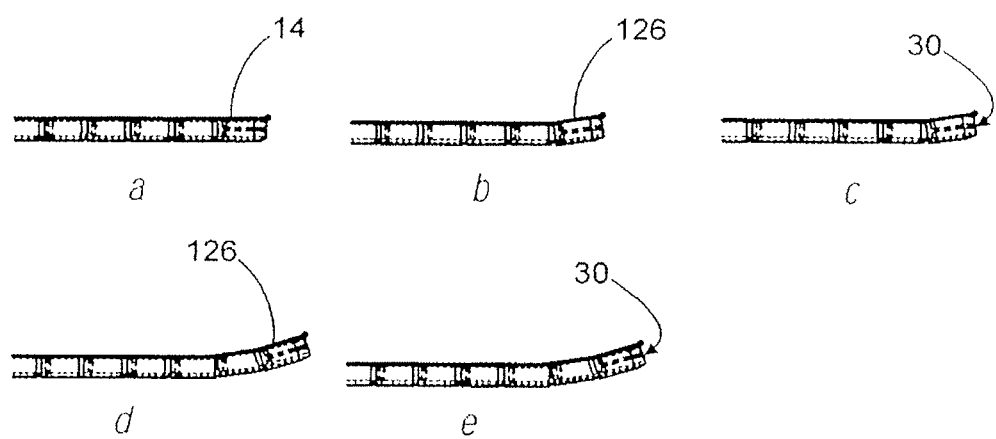
FIG. 10 illustrates various embodiments of a motion sequence of the device of FIG. 1.

FIG. 10 illustrates various embodiments of a motion sequence of the steerable multi-linked device 10. At the start of the sequence, the second mechanism 14 surrounds the first mechanism 12 as shown in step "a" of FIG. 10, the longitudinal axes 38, 62, 90 of the links 28, 30, 32 of the first mechanism 12 are substantially aligned with the respective longitudinal axes 134, 164, 212 of the links 124, 126, 128 of the second mechanism, and the second end 26 of the first mechanism 12 is at substantially the same position as the second end 122 of the second mechanism 14. A tensioning cable is pulled tight, thereby placing the first mechanism 12 in the rigid mode. The steering cables are not pulled tight, thereby placing the second mechanism 14 in the limp mode.

The second mechanism 14 is then advanced so that its second link 126 is positioned approximately one link ahead of the second end 24 of the first mechanism 12 as shown in step "b" of FIG. 10. The cables 16, 18, 20 may be utilized to orient the second link 126 to a particular orientation, where the longitudinal axis 134 of the first link 124 is no longer aligned with the longitudinal axes 164 of the intermediate links 128 of the second mechanism 14 or the longitudinal axis 90 of the second link 30 of the first mechanism 12. After the second link 126 is in the desired position and orientation, the steering cables are pulled with identical force in order to place the second mechanism 14 in the rigid mode, thereby preserving the position and orientation of the second mechanism 14.

The pulling force of the tensioning cable is then released to place the first mechanism 12 in the limp mode. After the first mechanism 12 is placed in the limp mode, the first mechanism 12 is advanced so that its second link 30 is at substantially the same position as the second end 122 of the second mechanism 14 as shown in step "c" of FIG. 10. After the second link 30 of the first mechanism 12 is in the desired position and orientation, the tensioning cable is pulled tight to place the first mechanism 12 back in the rigid mode, thereby preserving the position and orientation of the first mechanism 12.

The pulling forces of the steering cables are then released to place the second mechanism 14 back in the limp mode. After the second mechanism 14 is placed back in the limp mode, the second mechanism 14 is advanced so that its second link 126 is once again positioned approximately one link ahead of the second end 26 of the first mechanism 12 as shown in step "d" of FIG. 10. After the second link 126 is in the desired position and orientation, the steering cables are pulled with identical force in order to place the second mechanism 14 in the rigid mode, thereby preserving the position and orientation of the second mechanism 14.

The pulling force of the tensioning cable is then released to place the first mechanism 12 back in the limp mode. After the first mechanism 12 is placed back in the limp mode, the first mechanism 12 is advanced so that its second link 30 is once again at substantially the same position as the second end 122 of the second mechanism 14 as shown in step "e" of FIG. 10. After the second link 30 of the first mechanism 12 is in the desired position and orientation, the tensioning cable is pulled tight to place the first mechanism 12 back in the rigid mode, thereby preserving the position and orientation of the first mechanism 12. The general motion sequence described hereinabove, may be repeated any number of times, and the second link 126 of the second mechanism 14 may be advancing in any direction and orientation.

One skilled in the art will appreciate that any number of motion sequences may be utilized with the multi-linked device 10. For example, according to various embodiments, the second mechanism 14 may advance any number of links ahead of the first mechanism 12.

The exemplary sizes described hereinabove are generally relative to each other, and one skilled in the art will appreciate that the multi-linked device 10 can be scaled up or scaled down. For example, although the diameter at the largest portion of the intermediate link 128 of the multi-linked device 10 is on the order of approximately 9.65 millimeters for the embodiments described hereinabove, one skilled in the art will appreciate that, for other embodiments, the intermediate link 128 can be scaled down such that the diameter at the largest portion of the intermediate link 128 of the multi-linked device 10 is on the order of approximately 1.0 millimeter. For such embodiments, each of the other components of the multi-linked device 10 would also be proportionally scaled down.

Figure 11:
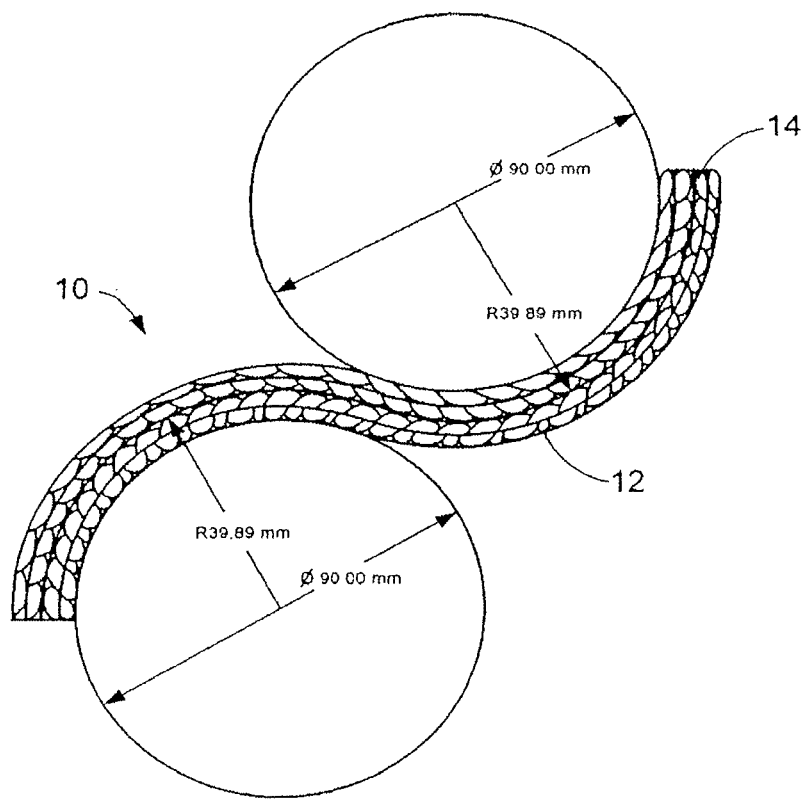
FIG. 11 illustrates various embodiments of a steerable multi-linked device traversing a path having tight curvatures.

The combination of the unique configuration of the respective links 28, 30, 32 which comprise the first mechanism 12 and the unique configuration of the respective links 124, 126, 128 which comprise the second mechanism 14 provides the multi-linked device 10 with the ability to traverse a path defined by the circumference of a circle having a relatively small radius. For example, for the exemplary sizes described hereinabove, the multi-linked device 10 can traverse a path defined by the circumference of a circle having a radius on the order of approximately 45 millimeters. An example of the multi-linked device 10 navigating such tight curvatures is shown in FIG. 11. For embodiments, where the largest portion of the intermediate link 128 of the multi-linked device 10 is on the order of approximately 1.0 millimeter, the multi-linked device 10 can traverse a path defined by the circumference of a circle having a radius significantly smaller than 45 millimeters. One skilled in the art will appreciate that the ability to navigate such tight curvatures makes the multi-linked device 10 suitable for use in a number of different minimally invasive procedures, both in luminal spaces and in intracavity spaces.

Figure 12:
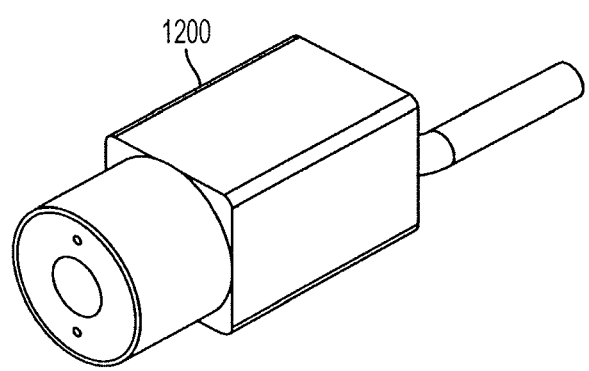
FIG. 12 illustrates an exemplary camera according to an embodiment.

In an embodiment, the flexible, articulated device 10 may include a visualization system. The visualization system may include one or more cameras, such as a charge-coupled device ("CCD") camera, a complimentary metal-oxide semiconductor ("CMOS") camera and/or the like. In an embodiment, one or more wires may electronically connect a camera to a display device, such as a video monitor, a computer display and/or the like. In other embodiment, the camera or the articulated device 10 may include a wireless transmitter for communication with a remote display. In an embodiment, multiple cameras or other sensors (such as audio sensors) may be used to provide additional capabilities. For example, a stereo camera system may be used to provide augmented stereoscopic vision. FIG. 12 illustrates an exemplary camera 1200 according to an embodiment.

Figure 13A:
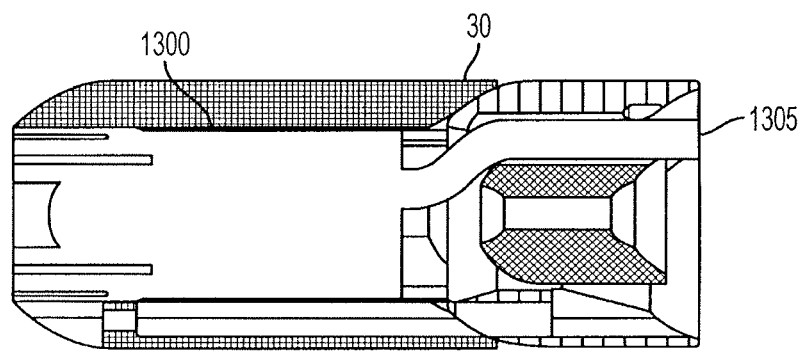
FIGS. 13A and 13B illustrate an exemplary camera housed in a link according to an embodiment.
Figure 13B:
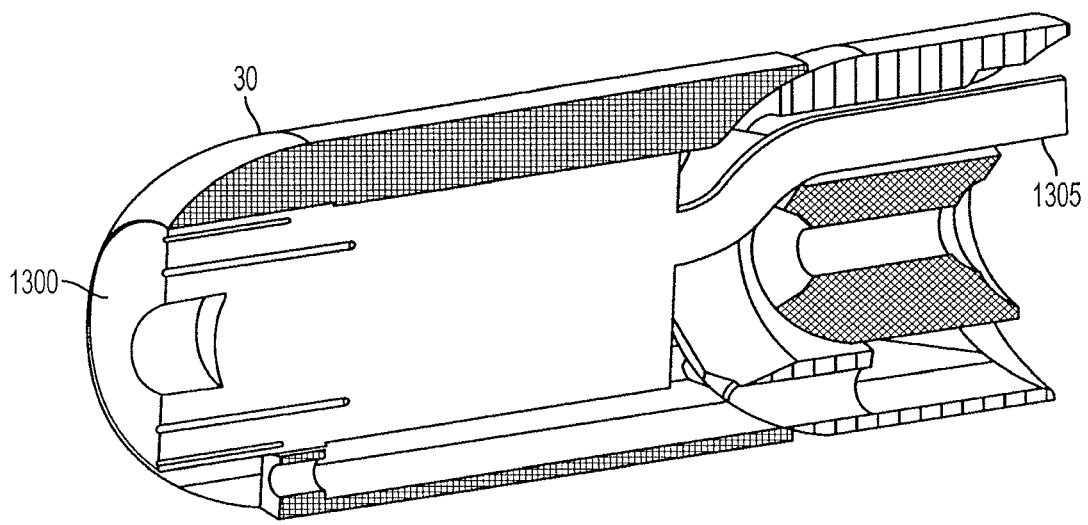

In an embodiment, the camera may be mounted distally on the articulated device 10. For example, the camera may be housed in a second link 30 as illustrated in FIGS. 13A and 13B. In an embodiment, a camera system 1300 may be fastened to the second link 30 by one or more screws, an adhesive, a press-fit, or in any other suitable manner. As used herein, a camera system may include a single camera or multiple cameras to provide stereoscopic vision.

In an embodiment, the second link 30 may define one or more ports, such as a first port 222, a second port 224, and a third port 226. The camera 1300 may occupy at least a portion of the second link 30. The camera may be mounted to the link or it may occupy one or more of the ports. In an embodiment, one or more wires 1305 for the transmission of electrical signals may be connected to the camera 1300 and may occupy one or more ports 222, 224, 226. In an embodiment, the one or more wires 1305 may extend from the second link 30 to a feeder mechanism via the one or more ports 222, 224, 226. Alternatively, the camera may transmit images via a wireless signal. In such an embodiment, no cables may be connected to the camera or may occupy a port. The feeder mechanism may be positioned at or near the proximal end of the articulated device to mechanically feed cameras, wires, and/or other equipment through the ports, or to feed the cables through the inner or outer articulated device in order to move the device.

Figure 16:
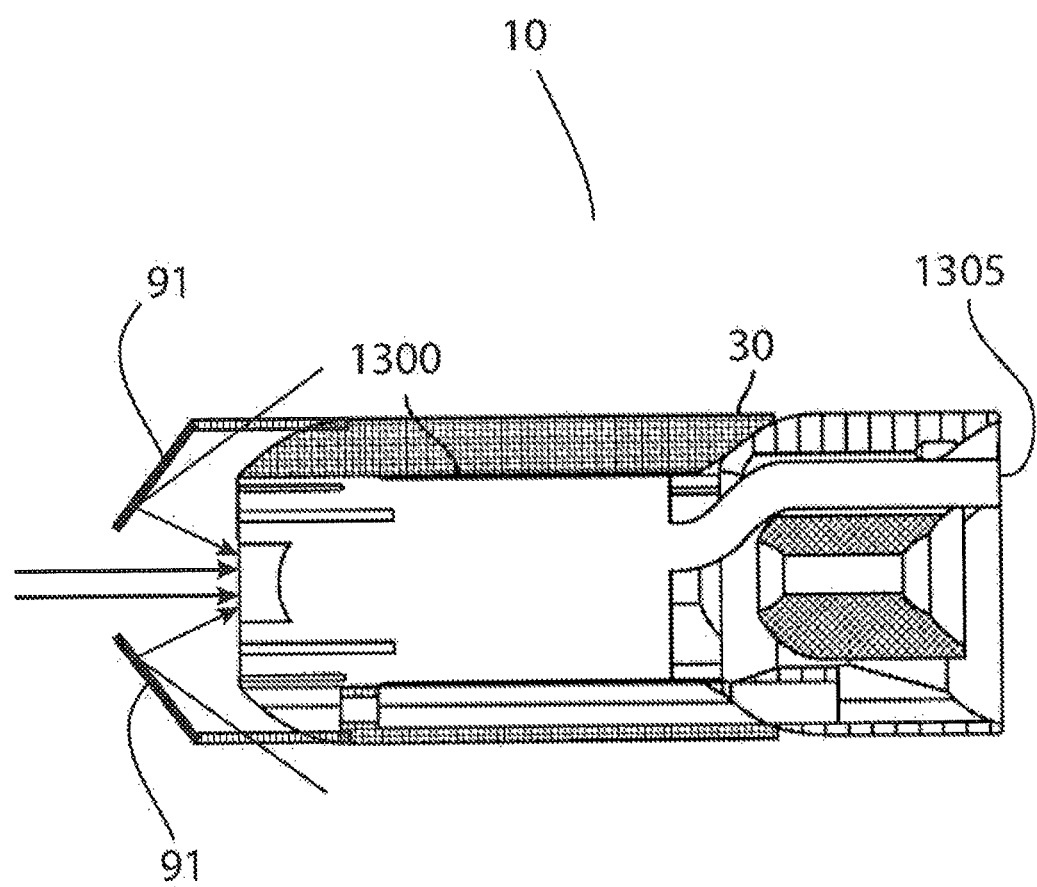
FIG. 16 illustrates example mirrors according to an embodiment.

In an embodiment, the articulated device 10 may include one or more mirrors whose reflective surface may be positioned within the view of the camera 1300. For example, as illustrated by FIG. 16, the mirrors 91 may be mounted on the second link 30 in such a way to allow the camera 1300 to transmit images of an area surrounding the device 10, such as an area located to the side of and/or behind the camera. This mirrored configuration may allow a user of a articulated device 10 to view areas that are not located in direct view of the camera 1300.

In an embodiment, the second link 30 may include a protective shield. The protective shield may be fabricated from plastic, glass and/or any other suitable material. In an embodiment, the protective shield may be secured to the second link 30 in any suitable manner, including, but not limited to by a snap-fit connection, an adhesive connection and/or the like. In an embodiment, the protective shield may be secured to the distal end of the second link 30. The protective shield may be substantially spherical, oval, cylindrical, dome or otherwise shaped. Optionally, the protective shield may exhibit optical properties. For example, a protective optical shield may be made of a material having an internal or external transmittance, surface reflectance, and/or refractive index that enhances the ability of the camera system to obtain images. The shield may also have an inner or outer surface having a concave or convex radius of curvature to magnify or reduce certain images received by the camera system.

Figure 15A:
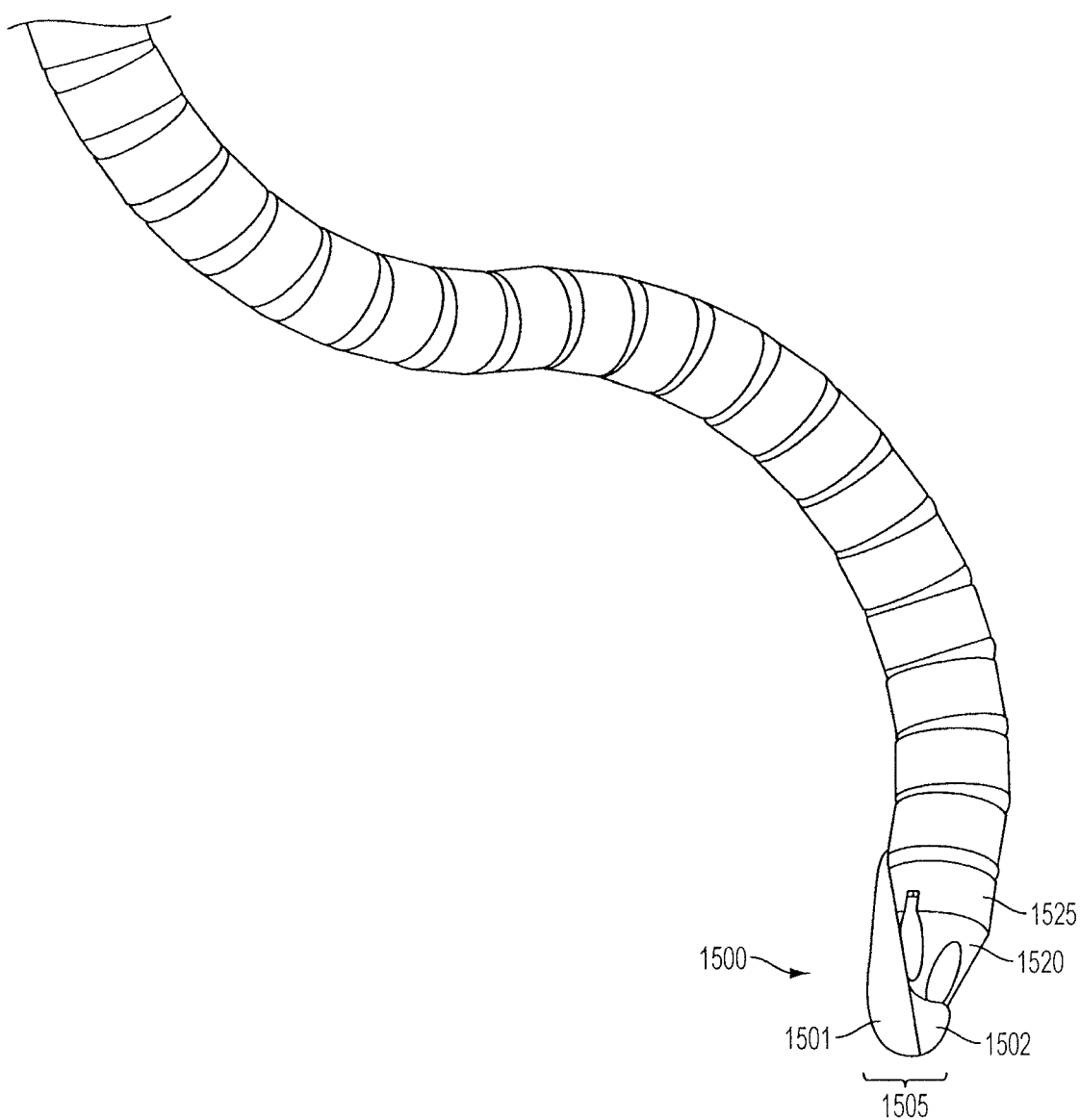
FIGS. 15A and 15B illustrate an exemplary protective shield according to an embodiment.
Figure 15B:
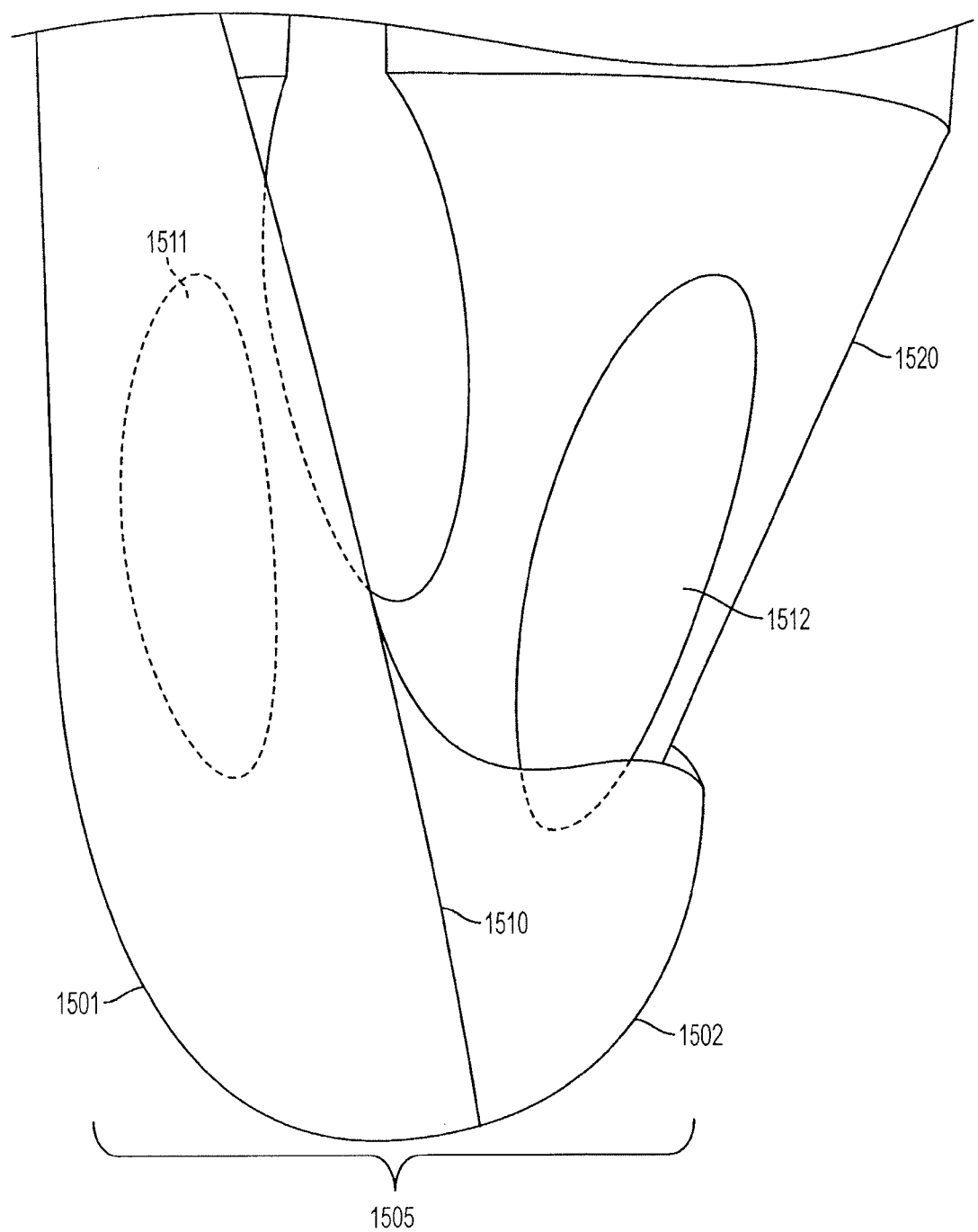

FIGS. 15A and 15B illustrate an exemplary protective shield according to an embodiment. As illustrated by FIGS. 15A and 15B, the protective shield 1500 may include a first shield section 1501 that fully covers at least one port 1511 and a second shield section 1502 that leaves a substantial portion of at least one port 1512 exposed. The first shield section 1501 extends along a side of the device's tip and extends along at least a portion of the device's body 1525, such as the second link 30 of the multi-linked device. The first shield section and second shield section are connected at a seam 1510 and together may provide a blunt leading surface 1505 that may protect against the damage of tissue or other surroundings. In an embodiment, the protective shield 1500 may have a spade-like shape if for example, it is being used to assist in blunt dissection of facial planes. The protective shield 1500 may be shaped to minimize glare from an integrated light guide or other similar light source. The protective shield 1500 also may provide beneficial optical properties, such as by increasing the field of view.

In an embodiment, the protective shield 1500 may be filled with a fluid, such as air, water, oil and/or the like. The fluid may serve to magnify the image of the region being viewed. The fluid may also mitigate adverse visual conditions such as condensing moisture on the inside and/or outside of the shield.

In an embodiment, the protective shield may be used in conjunction with one or more image fibers enclosed in a sheath. A sheath may be a catheter, shaft or the like. The sheath enclosed image fibers may occupy one or more ports 222, 224, 226 of the device, and may extend from a proximal end of the device 10 to a distal end of the device 10. The distal end of the device may include a protective shield such as that described above.

In an embodiment, the sheath may include one or more mirrors. The mirrors may be mounted on the sheath in such a way to allow the image fibers to transmit images of an area surrounding the device 10, such as an area located to the side of and/or behind the image fibers. This mirrored configuration may allow a user of an articulated device 10 to view areas that are not located in direct view of the image fibers.

In an embodiment, the protective shield may surround at least a portion of a camera 1300, one or more image fibers and/or the like. As such, the protective shield may provide a barrier between the camera 1300, one or more image fibers and/or the like and an area exterior to the device 10. The protective shield may allow viewing of the exterior area at an optimal focal distance. For example, the shield may maintain a proper separation between the camera 1300 and/or other optical components and the exterior region to allow viewing of the region at a proper distance. In an embodiment, the optimal focal distance may be between approximately 6 mm and 10 mm, with a depth of field to infinity. The field of view may be a cone that may be at least +/−35 degrees.

Figure 17:
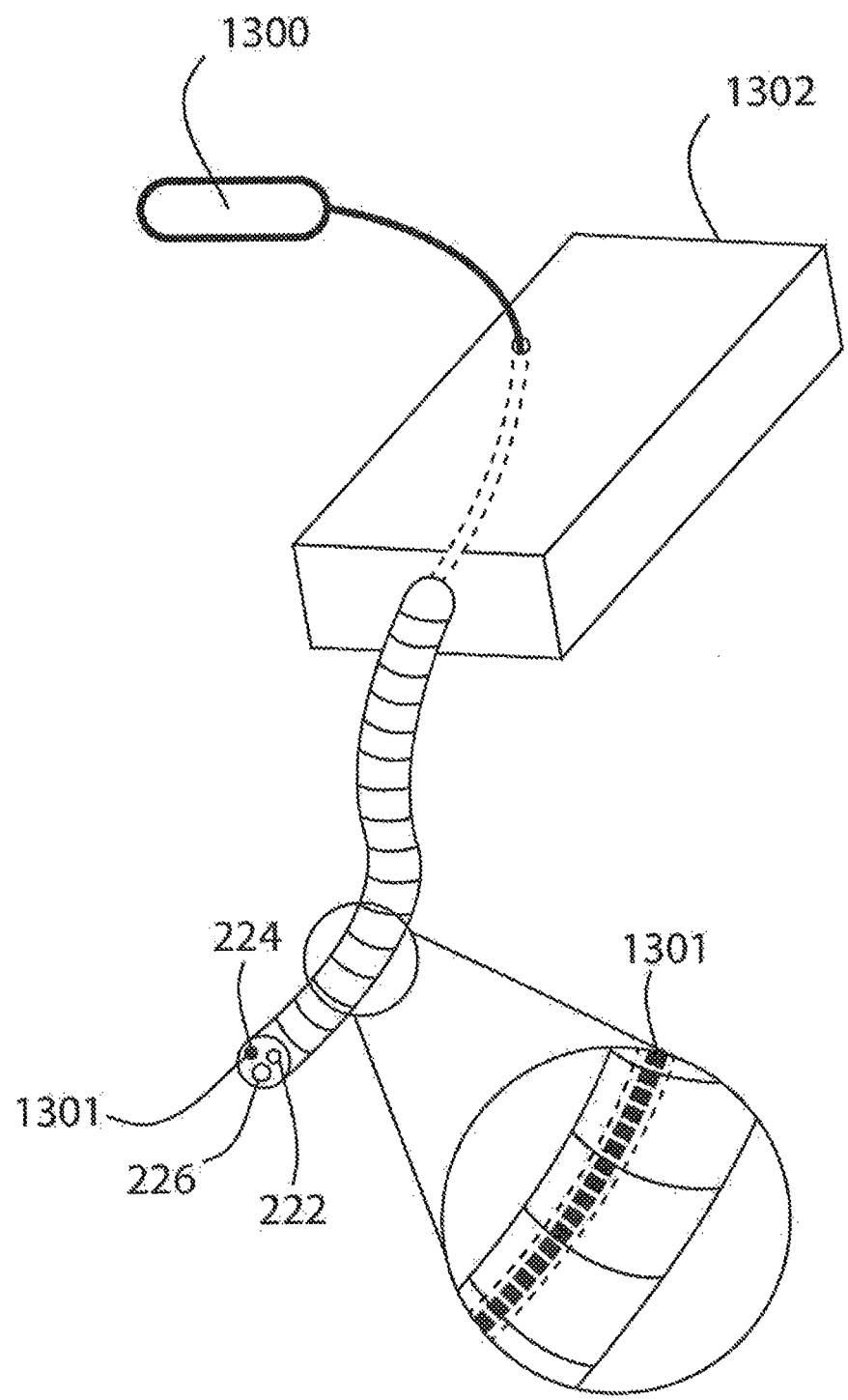
FIG. 17 illustrates example fiber optics connected to a camera according to an embodiment.

In an embodiment, a camera may be mounted on the feeder 1302 of the articulated device 10 and positioned to be fed to the proximal end of the articulated device. For example, the camera may be mounted on the feeder mechanism 1302. In an embodiment, one or more image fibers 1301, such as fiber optics, may be connected to the camera 1300 as illustrated for example in FIG. 17. The one or more image fibers may occupy one or more ports 222, 224, 226 of the device 10, and may extend from a proximal end of the device 10 to a distal end of the device 10 and into the feeder. In an embodiment, the image fibers may include an integrated light guide. In an embodiment, a protective shield, may be fastened to a distal end of the second link 30 in any suitable manner.

Figure 14B:
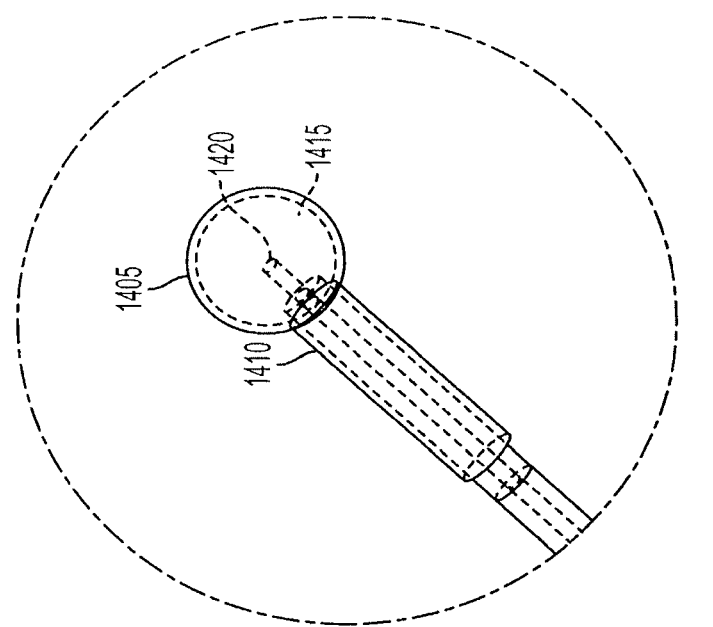
FIG. 14B illustrates an exemplary sheath and protective shield filled with a fluid according to an embodiment.
Figure 14A:
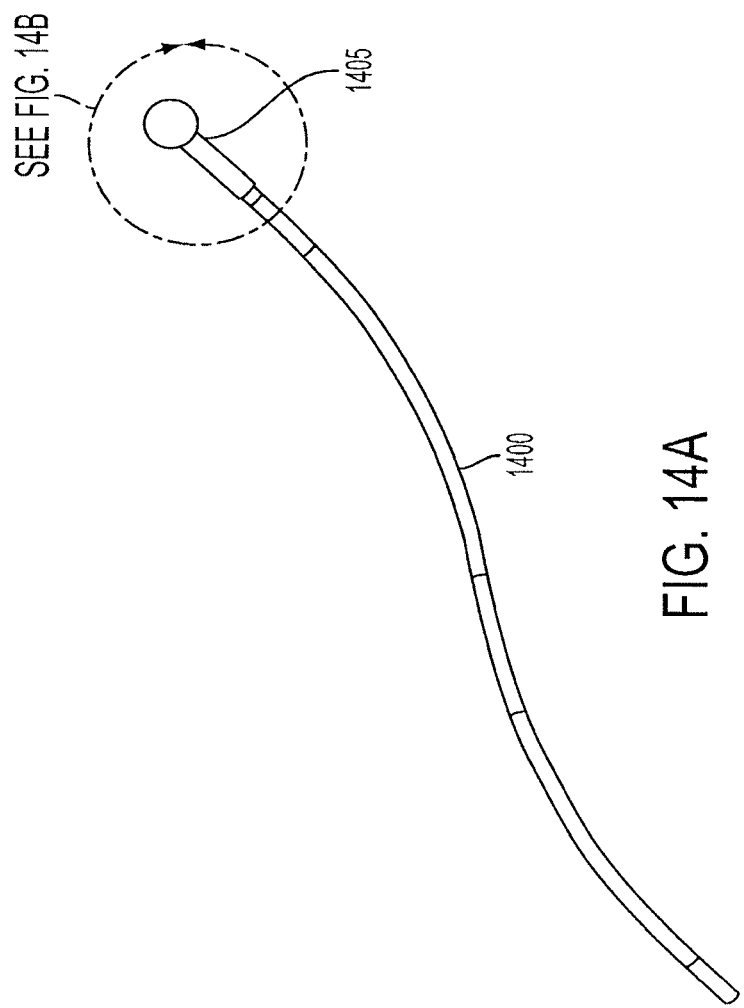
FIG. 14A illustrates one or more image fibers enclosed by an exemplary sheath according to an embodiment.

In an embodiment, one or more image fibers may be enclosed by a sheath 1400, such as a catheter, shaft and/or the like as illustrated by FIGS. 14A and 14B. The sheath enclosed image fibers 1420 may occupy one or more ports 222, 224, 226 of the device 10, and may extend from a proximal end of the device 10 to a distal end of the device 10. In an embodiment, the sheath 1400 may provide protection for the image fibers 1420. In addition, the sheath 1400 may be steerable to provide added maneuverability to the visualization system. In an embodiment, a protective shield 1405 may be fastened to a distal end 1410 of the sheath 1400 in any suitable manner.

In an embodiment, the sheath 1400 and protective shield 1405 may be filled with a fluid 1415, such as air, water, oil and/or the like. The fluid 1415 may serve to magnify the image of the region being viewed. The fluid 1415 may also mitigate adverse visual conditions such as condensing moisture on the inside and/or outside of the shield 1405.

While several embodiments of the invention have been described herein by way of example, those skilled in the art will appreciate that various modifications, alterations, and adaptations to the described embodiments may be realized without departing from the spirit and scope of the invention defined by the appended claims.

The invention claimed is:

1. An articulated device, comprising:
   a first steerable multi-linked mechanism; and
   a second steerable multi-linked mechanism comprising:
      a first link,
      a plurality of intermediate links, wherein a first one of the intermediate links is movably coupled to the first link,
      a second link movably coupled to a second one of the intermediate links, and
      a camera located within at least a portion of the second link,
   wherein the second steerable multi-linked mechanism is configured to concentrically surround the first steerable multi-linked mechanism,
   wherein the second steerable multi-linked mechanism is configured to operate in a rigid mode when the first steerable multi-linked mechanism operates in a limp mode,
   wherein the second link comprises a plurality of mirrors, wherein a reflective surface of each of the mirrors is positioned to reflect an image of at least one of an area located behind the camera or an area located to a side of the camera, wherein each reflective surface is within direct view of the camera.

2. The articulated device of claim 1, wherein the second link defines one or more ports, wherein one or more wires connected to the camera occupy one or more of the ports.

3. The articulated device of claim 2, wherein the one or more wires extend from the second link to a feeder mechanism via at least one of the one or more ports.

4. The articulated device of claim 1, wherein the camera is configured to transmit images of the area behind the camera and the area to the side of the camera using the mirror when:
   the second steerable multi-linked mechanism operates in the rigid mode and the first steerable multi-linked mechanism operates in the limp mode; and
   the second steerable multi-linked mechanism operates in the limp mode and the first steerable multi-linked mechanism operates in the rigid mode.

5. The articulated device of claim 1, wherein the second link further comprises a protective shield connected to a distal end of the second link, wherein the protective shield surrounds at least a portion of the camera.

6. The articulated device of claim 5, wherein the protective shield comprises at least one blunt surface.

7. The articulated device of claim 5, wherein the protective shield comprises a liquid.

8. The articulated device of claim 1, wherein the second link further comprises:
   a first port and a second port, and
   a protective shield connected to a distal end of the second link, wherein the protective shield comprises:
      a first shield section that fully covers the first port, and
      a second shield section that covers a portion of the second port.

* * * * *